United States Patent [19]
Choi

[11] Patent Number: 5,971,963
[45] Date of Patent: Oct. 26, 1999

[54] PORTABLE AUTOMATIC SYRINGE DEVICE AND INJECTION NEEDLE UNIT THEREOF

[76] Inventor: Soo Bong Choi, Youwan Apt. #5-908, 421-7, Yeosnoo-dong, Chung-shi, Chungcheongbuk-do, Rep. of Korea

[21] Appl. No.: 09/243,286

[22] Filed: Feb. 2, 1999

Related U.S. Application Data

[62] Division of application No. 09/136,002, Aug. 18, 1998.

[51] Int. Cl.$^6$ ............................. A61M 5/00; A61M 25/02
[52] U.S. Cl. .................................. 604/177; 128/DIG. 26; 604/180
[58] Field of Search ................................. 604/174, 177, 604/180, 272; 128/DIG. 26

[56] References Cited

U.S. PATENT DOCUMENTS

| | | | |
|---|---|---|---|
| 2,734,604 | 7/1956 | Crescas et al. | 604/155 |
| 2,786,468 | 3/1957 | Singer et al. | 604/155 |
| 3,336,925 | 8/1967 | Thompson, III | 604/155 |
| 3,631,847 | 1/1972 | Hobbs, II | 604/155 |
| 4,235,234 | 11/1980 | Whitney et al. | 604/177 |
| 4,342,311 | 8/1982 | Whitney et al. | 604/155 |
| 4,389,210 | 6/1983 | Genese | 604/177 |
| 4,611,382 | 9/1986 | Clark | 604/177 |
| 4,645,492 | 2/1987 | Weeks | 604/180 |
| 4,710,176 | 12/1987 | Quick | 604/180 |
| 4,731,058 | 3/1988 | Doan | 604/155 |
| 4,743,231 | 5/1988 | Kay | 604/177 |
| 4,769,010 | 9/1988 | Fenton, Jr. | 604/180 |
| 4,978,335 | 12/1990 | Arthur, III | 604/155 |
| 5,108,376 | 4/1992 | Bonaldo | 604/177 |
| 5,147,319 | 9/1992 | Ishikawa et al. | 604/174 |
| 5,269,762 | 12/1993 | Armbruster et al. | 604/155 |
| 5,370,627 | 12/1994 | Conway | 604/180 |
| 5,409,466 | 4/1995 | Watson et al. | 604/180 |
| 5,647,853 | 7/1997 | Feldman et al. | 604/155 |
| 5,690,616 | 11/1997 | Mogg | 604/174 |

*Primary Examiner*—Paul J. Hirsch
*Attorney, Agent, or Firm*—Ladas & Parry

[57] ABSTRACT

A portable automatic syringe device having a configuration including a separable rotating shaft adapted to provide a drive force to a piston included in the automatic syringe device so that the rotating shaft can be separated, along with the piston, from a housing of the syringe device upon re-filling a syringe of the syringe device with a liquid medicine. A coupling member is coupled between the rotating shaft and power transmission means. The coupling member has a reduction gear engaging with an output gear of the power transmission means, and a cross groove. A horizontal engaging pin is fixed to a lower end of the rotating shaft in such a fashion that it is engaged in the cross groove when the rotating shaft is positioned in position in the syringe device, thereby causing the rotating shaft to be coupled to the coupling member. An injection needle unit is also provided which includes an "L" shaped injection needle member provided with a curved portion capable of absorbing impact, thereby preventing a breakage of the injection needle member. The injection needle unit also includes a sensor for sensing an abnormal blood sugar level generated due to an abnormal injection of a liquid medicine.

2 Claims, 22 Drawing Sheets

PORTABLE AUTOMATIC SYRINGE DEVICE AND INJECTION NEEDLE UNIT THEREOF

This application is a divisional of copending application number 09/136,002 filed on Aug. 18. 1998.

BACKGROUND OF THE INVENTION

1. Field of the Invention

The present invention relates to a portable automatic syringe device enabling an injection of liquid medicine for a prolonged time and an injection needle unit thereof, and more particularly to a portable automatic syringe device having a configuration including a separable rotating shaft adapted to provide a drive force to a piston included in the automatic syringe device so that the rotating shaft can be separated, along with the piston, from a housing of the syringe device upon re-filling a syringe of the syringe device with a liquid medicine, and set in position in the housing after the re-filling of the liquid medicine. The present invention also relates to an injection needle unit including an injection needle member provided with a curved portion capable of absorbing impact. The present invention further relates to an injection needle unit including an injection needle member provided with a glucose sensor, and a portable automatic syringe device using the injection needle member.

2. Description of the Prior Art

Automatic syringe devices, which enable an injection of liquid medicine for a prolonged time, are well known. Typically, known automatic syringe devices have a configuration in which a push means for pushing a syringe piston is coupled to a housing receiving an injection syringe. For example, such automatic syringe devices are disclosed in and U.S. Pat. No. 4,417,889. The syringe device disclosed in Japanese Utility Model Laid-open Publication No. Sho. 52-3292 has inconvenience in carrying it because it has an injector mounted outside a basic case, thereby requiring a double case structure. In order to solve such a disadvantage, an automatic syringe device requiring no double case structure has been proposed, as in the above mentioned U.S. Pat. No. 4,417,889. FIGS. 1 and 2 illustrate a control circuit and a structure of the automatic syringe device disclosed in U.S. Pat. No. 4,417,889, respectively. Referring to FIG. 1, the output of an oscillator Al is coupled to a timer A2 which is, in turn, coupled at its output to a digital comparator A3. The digital comparator A3 also receives an output from a fixed number switch A4. The output of the digital comparator A3 is connected to a counter A6 and an R/S flip-flop A9. Another oscillator A5 is also provided which has an output coupled to counters A6 and A13, and AND gates A10 and A11. The flip-flop A9 is reset by an output from a digital comparator A7. Another R/S flip-flop A16 is also provided which is reset by an output from a digital comparator A14 coupled to the counter A13. A control unit A17 is also coupled to the counter A13. The control unit A17 serves to activate the counter A13 in accordance with an operation of a manual infusion switch A12. The control unit A17 applies its output to the counters A13 and A16. The output from the control unit A17 is also sent to a counter A21. The output of the counter A21 is coupled to a digital comparator A22 which is, in turn, coupled to a step motor driver A19 for driving a step motor A20. The output of the flip-flop A16 is coupled to one input of the AND gate A11, which is also coupled at the other input thereof to the oscillator A5. The output of the AND gate A11 is coupled to one input of an OR gate A18. Fixed number switches A15 and A25 are connected to the digital comparators A14 and A22, respectively. Each of the fixed number switches A4, A8, A15, and A25 has five protruding insert bars and serves to provide a reference value for an associated one of the digital comparators A3, A7, A14, and A22. A light source A24 and a photo sensor A23 are coupled to the counter A21 in order to provide sensing results thereof to the counter A21, respectively. Referring to FIGS. 2 and 3, the arrangements of the light source A24 and photo sensor A23 are illustrated. As shown in FIGS. 2 and 3, the light source A24 and photo sensor A23 are arranged in such a fashion that they face each other while being vertically spaced from each other. A gear plate, which is included in a gear mechanism G. is interposed between the light source A24 and photo sensor A23. The gear plate has a plurality of through holes A26 uniformly spaced from one another in a circumferential direction, as shown in FIG. 3. The gear plate is fixedly fitted around a gear shaft A27 having a screw portion. A piston plate A28 is threadedly coupled to the gear shaft A27 in the form of a nut in such a fashion that it slides along the screw portion of the gear shaft A27 when the gear shaft A27 rotates. The rotation of the gear shaft A is carried out by a drive force from the motor A20 transmitted via the gear mechanism G. The driving of the motor A20 is controlled by the operations of the counter A21, digital comparator A22, switch A25, and motor drive A19. All the above mentioned elements of the syringe device are received in a housing. In particular, the light source A24 and photo sensor A23 are fixedly mounted at an upper portion of the housing by means of a bracket fixed to the housing. In this syringe device, a liquid medicine, such as insulin, contained in a syringe I is outwardly injected through an injection needle N connected to the syringe I, by a slide movement of the piston plate A28. In such a syringe device, however, the housing and syringe I thereof are exposed to ambient air. As a result, moisture and water are likely to penetrate into the syringe device. For this reason, there is inconvenience in that if the user desires to take a shower while the syringe is in place, then the housing should be contained in a separate sealing case.

In order to solve such a problem, a sealable syringe device has been proposed by the applicant. Such a sealable syringe device is illustrated in FIG. 4 which is a front view. Referring to FIG. 4, the syringe device includes a cover 10 sealably coupled to the upper end of a housing 10, and a bottom cover 40 sealably coupled to the lower end of the housing 10. A connector 2, to which a feeding tube is integrally connected, is threadedly coupled to the cover 10. The connector 2 communicates with a syringe 21 received in the housing 10. A piston 22 is slidably fitted in the syringe 21. A liquid medicine to be syringed is contained in the syringe 21. A power transmission means 30 is mounted on the bottom surface of the housing 20. The power transmission means 30 has a rotating shaft 31 to which a disc type push means 50 is threadedly coupled. The disc type push means 50 moves vertically by a rotation of the rotating shaft 31, thereby vertically moving the piston 22.

Referring to FIG. 5, which is a plan view of FIG. 4, the cover 10, to which the connector 2 connected with the feeding tube 1 is connected, is arranged on the left portion of the upper surface of the housing 20. A battery cover 24 is arranged on the right portion of the upper surface of the housing 20.

FIG. 6 is a cross-sectional view taken along the line A—A of FIG. 5. As shown in FIG. 6, the cover 10 is centrally provided with a threaded hole 11 in which the connector 2 is threadedly fitted at its lower end. The cover 10 is also provided at its lower end with a bolt portion 12 threadedly fitted in the upper end of the housing 20. A packing 13 is fitted around the bolt portion 12 of the cover 10 between the lower end of the cover 10 and the upper end of the housing 20. A syringe receiving chamber 23 is defined in the interior of the housing 20. The push means 50 is fitted in the lower end of the housing 20 in such a fashion that it slides vertically in the housing 20. The housing 20 is also formed at its inner surface with a vertical push means guide groove 25 adapted to guide a vertical movement of the push means 50 and vertical piston guide grooves 27 adapted to guide a vertical movement of the piston 22.

FIG. 7 shows a detailed configuration of the push means 50 threadedly coupled to the rotating shaft 31 of the power transmission means 30, along with a detailed configuration of the power transmission means 30. As shown in FIG. 7, the push means 50 includes a lower disc 54 threadedly coupled to the rotating shaft 31 in such a fashion that it slides vertically along the rotating shaft 31. The lower disc 54 is provided at its periphery with a guide protrusion 51 engaged in the guide groove 25 of the housing 20 and adapted to guide the vertical movement of the lower disc 54. The push means 50 also includes an upper disc 55 integrally formed with the lower disc 54. The upper disc 55 is provided at its periphery with an engagement means 52. The upper disc 55 is fitted in a sleeve plate 26 fixed to the lower end of the piston 22 in such, a manner that its engagement means 52 engages with a mating engagement means formed on the inner peripheral surface of the sleeve plate 26. The sleeve plate 26 is also provided at its outer peripheral surface with protrusions engaging with the guide grooves 27 respectively. The power transmission means 30 includes a reduction mechanism 33 for transmitting the rotating force of a motor (not shown) to the rotating shaft 31 in a speed-reduced manner.

In order to use the syringe device having the above mentioned configuration, the piston 22, which is in a state separated from the housing 20, is first fitted in the syringe 21 which is also in a state separated from the housing 20, in such a manner that it is completely inserted into the syringe 21. In this state, a disposable injection needle (not shown) is fitted onto the tip 21-1 of the syringe 21. Thereafter, the injection needle is penetrated into the interior of a phial through the plug of the phial. In this state, the piston 22 is pulled to suck a liquid medicine (for example, insulin) contained in the phial into the syringe 21.

The piston 22, which is in a state fitted in the syringe 21 containing the liquid medicine, is then inserted into the syringe receiving chamber 23 of the housing 20 in such a manner that it is seated on the push means 50. Subsequently, the cover 10 is threadedly coupled to the upper end of the housing 23. The connector 2 is then threadedly fastened to the cover 10. As the connector 2 is threadedly fastened to the cover 10, it is fitted onto the syringe tip 21-1. Thus, the syringe 21 is maintained in a sealed state in the housing 20. When the motor (not shown) drives under the above condition, the push means 50 moves upwardly, thereby upwardly pushing the piston 22. As a result, the liquid medicine contained in the syringe 21 is outwardly injected from the syringe 21. At this time, the upward movement of the push means 50 is accurately carried out because its guide protrusion 51 engages with the guide groove 25. Since the engagement means 52 of the push means 50 engages with the mating engagement means of the sleeve plate 26 integrally formed with the lower end of the piston 22, the upward movement of the piston 22 is also accurately carried out.

In such a syringe device, it is necessary to set the initial height or vertical position of the lower disc 54 of the push means 50 every time the syringe 21 filled with a liquid medicine is inserted into the housing 20, in order to allow the piston 22 to be accurately seated on the upper disc 55 of the push means 50. However, it is difficult to accurately set a desired initial vertical position of the lower disc 54.

Meanwhile, FIG. 9 illustrates an example of a conventional injection needle unit used for portable automatic syringe devices enabling a prolonged injection of a liquid medicine. As shown in FIG. 9, the injection needle unit includes a feeding tube 1, a "-" shaped straight injection needle member (called a "straight butterfly-shaped injection needle") 3 connected to one end of the feeding tube 1, and a connector 2 connected to the other end of the feeding tube 1.

In order to use such an injection needle unit, the user himself slantly penetrates the injection needle member 3 into the subcutaneous tissue while observing the penetration of the injection needle member 3 with the naked eye. The reason why the user observes the penetration of the injection needle member 3 with the naked eye is because the injection needle member 3 has a straight shape. However, such an observation is very uncomfortable.

Furthermore, when the straight butterfly-shaped injection needle member 3 penetrates the subcutaneous tissue of the user on a slanted angle, its tip may be easily blocked by the subcutaneous tissue because the subcutaneous tissue is a multilayer tissue. As a result, the above mentioned conventional injection needle unit has a drawback in that it is difficult to smoothly inject the liquid medicine, namely, insulin.

The straight butterfly-shaped injection needle member 3 is also likely to move in the subcutaneous tissue of the user because it penetrates the subcutaneous tissue of the user on a slanted angle. In this case, the subcutaneous tissue may be damaged. In severe cases, blood may flow out of the subcutaneous tissue. The user may also feel a severe pain.

As mentioned above, the conventional injection needle unit has a drawback in that it is difficult to smoothly inject insulin because the injection needle member 3, which penetrates the subcutaneous tissue of the user on a slanted angle, may be easily blocked at its tip by the subcutaneous tissue. To this end, the feeding tube of such a conventional injection needle unit inevitably has an increased diameter. However, such a feeding tube having an increased diameter results in a possibility of an excessive insulin injection. In addition, this may result in wastage of expensive insulin. For instance, where it is desired to inject insulin into the user using an automatic syringe device equipped with the above mentioned injection needle unit, it is necessary to completely vent air existing in the feeding tube 1 and injection needle member 3 before penetrating the injection needle member 3 into the subcutaneous tissue of the user. To this end, insulin, which is contained in the syringe device, is outwardly discharged through the feeding tube 1 and injection needle member 3, thereby venting air. In this case, a large amount of insulin is wasted where the conventional injection needle unit having the diameter-increased feeding tube is used.

The use of such a diameter-increased feeding tube also results in an increase in the manufacturing costs.

In the case of the injection needle unit illustrated in FIG. 9, its connector 2 is simply fitted onto a connector portion 20-5 of the syringe device housing 20. For this reason, the connector 2 may be incidentally separated from the connector portion 20-5 of the housing 20.

In order to solve this problem, an injection needle unit has been proposed which has a configuration capable of preventing a separation of its connector. Such an injection needle unit is illustrated in FIGS. 10 and 11, respectively.

As shown in FIGS. 10 and 11, the injection needle unit includes a feeding tube 1, an injection needle member 3 connected to one end of the feeding tube 1, and a connector 2 connected to the other end of the feeding tube 1.

In the case of the injection needle unit shown in FIGS. 10 and 11, the injection needle member 3 has an "L" shaped injection needle 3-11. This injection needle 3-11 has a first portion, namely, a horizontal portion, fitted in a connecting rib 3-12 integrally formed with one end of the feeding tube 1, and a second portion, namely, a vertical portion, provided with a needle tip. The injection needle 3-11 is provided with a curved portion 3-13 at its horizontal portion fitted in the connecting rib 3-12, as shown in FIG. 11. A depressing member 3-14 is integrally formed with the connecting rib 3-12 in such a fashion that the injection needle 3-11 protrudes perpendicularly from the depressing member 3-14. The depressing member 3-14 is depressed against the skin of the user upon penetrating the injection needle member 3 into the subcutaneous tissue. A bacterial infection prevention member 3-14-1, which is made of a disinfected nonwoven fabric, is attached to the surface of the depressing member 3-14 which comes into contact with the skin of the user upon penetrating the injection needle unit 3 into the subcutaneous tissue. The feeding tube 1 of FIGS. 10 and 11 has a reduced diameter and an increased length, as compared- to that of FIG. 9. The connector 2, which is connected to the other end of the feeding tube 1, has a male thread 2-15. The connector 2 is protected by a protection cap 2-17 which has a female thread. 2-16 threadedly coupled to the male thread 2-15 of the connector 2. In use, the connector 2 is threadedly coupled to a connector portion 20-5 of a housing 20 included in an automatic insulin syringe device. The connector portion 20-5 of the housing 20 has a female thread 20-5a threadedly coupled to the male thread 2-15 of the connector 2. In FIG. 10, the reference numeral "3-18" denotes a needle protection cap.

Where it is desired to inject insulin contained in the automatic insulin syringe device using the above mentioned injection needle unit, the protection cap 2-17 is first separated from the connector 2, which is, in turn, threadedly coupled to the connector portion 20-5 of the housing 20. Thereafter, the needle protection cap 3-18 is separated from the injection needle 3-11. The user then penetrates the injection needle 3-11 into the subcutaneous tissue while depressing the depressing member 3-14 against the skin by fingers. At this time, the injection needle 3-11 penetrates vertically into the subcutaneous tissue of the user because it has an "L" shape. Accordingly, the user can carry out the penetration of the injection needle 3-11 instantaneously without any observation with the naked eye. Therefore, the user feels little pain upon penetrating the injection-needle 3-11 into the subcutaneous tissue. By virtue of such a configuration of the injection needle unit 3, the automatic insulin syringe device can be conveniently used, as shown in FIG. 13. Since the injection needle 3-11 penetrates vertically into the subcutaneous tissue of the user by virtue of its "L" shape, there is no phenomenon that the injection needle 3-11 is blocked at its tip by the subcutaneous tissue of the user. Thus, the injection of insulin is smoothly carried out. Accordingly, the feeding tube can have a reduced diameter and an increased length. Since the feeding tube 1 has a reduced diameter, it is possible to minimize the wastage of insulin occurring upon venting air existing in the feeding tube 1 and injection needle 3-11 and to reduce the manufacturing costs. Since the feeding tube 1 also has an increased length, it is possible to extend the range of the position of the injection needle 3-11 on the body of the user. Accordingly, it is possible to achieve convenience in use. Since the bacterial infection prevention member 3-14-1, which is made of a disinfected nonwoven fabric, is attached to the depressing member 3-14, it is possible to prevent the depressing member 3-14 from coming into direct contact with the skin of the user upon penetrating the injection needle unit 3 into the subcutaneous tissue. Accordingly, it is possible to prevent the user from being infected.

Since the injection needle 3-11 penetrates vertically into the subcutaneous tissue of the user by virtue of its "L" shape, as mentioned above, it hardly moves in the subcutaneous tissue, even when an external force is applied thereto. Accordingly, there is no damage of the subcutaneous tissue. Of course, there is no phenomenon that the blood flows out of the subcutaneous tissue. The user also does not feel any pain.

In the case of the injection needle unit mentioned above, the needle protection cap 3-18 is used which has a configuration as shown in FIG. 14. The needle protection cap 3-18 has a needle tip receiving hole including a smaller diameter portion 3-18-1 with the same diameter as the injection needle 3-11 and a larger diameter portion 3-18-2 with a diameter larger than the diameter of the injection needle 3-11. Since the needle protection cap 3-18 has such a configuration, there is a problem in that it is difficult to separate the needle protection cap 3-18 from the injection needle 3-11 because of the small diameter of the diameter portion 3-18-1. As a result, the injection needle 3-11 may be damaged. Since the smaller diameter portion 3-18-1 has a small diameter, a capillarity phenomenon may occur between the inner surface of the needle protection cap 3-18 and the outer surface of the injection needle 3-11 when the liquid medicine is outwardly discharged from the injection needle 3-11 to vent air,existing in the feeding tube 1 and injection needle 3-11. In this case, a part of the discharged liquid medicine is absorbed in the bacterial infection prevention member 3-14-1, thereby causing the user to be uncomfortable. The injection needle 3-11 has a sharp bent portion 3-11-1 between the vertical and horizontal portions thereof due to its "L"-shaped structure. This sharp bent portion 3-11-1 of the injection needle 3-11 may be subjected to excessive stress when the user moves excessively during injection. For instance, when the needle tip of the injection needle 3-11 moves from a position indicated by the solid line of FIG. 15 to a position indicated by the phantom line of FIG. 15 as the user exercises or conducts hard work, or due to other reasons, the sharp bent portion 3-11-1 of the injection needle 3-11 may be subjected to excessive stress. In this case, the injection needle 3-11 may be broken. For this reason, the reliability of the above mentioned injection needle unit is degraded.

SUMMARY OF THE INVENTION

The present invention has been made in view of the above mentioned problems involved in conventional automatic syringe devices and conventional injection needle units, and an object of the invention is to provide a portable automatic syringe device having a configuration including a separable rotating shaft adapted to provide a drive force to a piston included in the automatic syringe device so that the rotating shaft can be separated, along with the piston, from a housing of the syringe device upon re-filling a syringe of the syringe device with a liquid medicine, and set in position in the housing, after the re-filling of the liquid medicine, while observing the setting operation with the naked eye.

Another object of the invention is to provide a portable automatic syringe device having a configuration including a reset button made of a semi-permeable material capable of preventing penetration of moisture while allowing ventilation of air, thereby achieving an improvement in sealability while enabling a prolonged injection of a liquid medicine.

Another object of the invention is to provide an injection needle unit including an "L" shaped injection needle member provided with a curved portion capable of absorbing impact, thereby preventing a breakage of the injection needle member.

Another object of the invention is to provide an injection needle unit including a means for sensing an abnormal blood sugar level generated due to an abnormal injection of a liquid medicine.

Another object of the invention is to provide an injection needle unit including a means for sensing an abnormal blood sugar level generated due to an abnormal injection of a liquid medicine, thereby automatically controlling an automatic syringe device to which the injection needle unit is applied.

In accordance with one aspect, the present invention provides a portable automatic syringe device comprising a housing, a syringe separably received in the housing and contained with a liquid medicine, an injection needle unit coupled to the housing in such a fashion that it communicates with the syringe, a piston slidably fitted in the syringe and separably received in the housing, the piston being vertically movable in the syringe to inject the liquid medicine into the injection needle unit, a vertical rotating shaft having a screw extending throughout the length thereof, push means threadedly coupled to the screw of the rotating shaft in such a fashion that it moves along the rotating shaft when the rotating shaft rotates, the push means being adapted to move the piston by the movement thereof, and power transmission means fixedly installed in the housing and adapted to transmit a drive force generated from power generating means to the rotating shaft, further comprising: coupling means for separably coupling said rotating shaft to said power transmission means, so that the rotating shaft is separable from said housing.

In accordance with another aspect, the present invention provides an injection needle unit usable in a portable automatic syringe device, the injection needle unit comprising a feeding tube, an "L" shaped injection needle member connected to one end of the feeding tube, a connector connected to the other end of the feeding tube, and a depressing member integrally formed with the injection needle member in such a fashion that the injection needle protrudes perpendicularly from the depressing member, the depressing member being depressed against the skin of a user upon penetrating the injection needle member into the subcutaneous tissue of the user, wherein the injection needle member comprises: a vertical injection needle provided with a needle tip; a horizontal connecting rib fitted in said one end of the feeding tube; and a curved portion connected between said injection needle and said connecting rib in such a fashion that it has a quadrant shape extending circumferentially about a center, flush with an upper end of the injection needle, said curved portion having a downward slant portion connected to the connecting rib.

In accordance with another aspect, the present invention provides an injection needle unit usable in a portable automatic syringe device, the injection needle unit comprising a feeding tube, an "L" shaped injection needle member connected to one end of the feeding tube, a connector connected to the other end of the feeding tube, and a depressing member integrally formed with the injection needle member in such a fashion that the injection needle protrudes perpendicularly from the depressing member, the depressing member being depressed against the skin of a user upon penetrating the injection needle member into the subcutaneous tissue of the user, further comprising: a glucose sensor attached to said injection needle and adapted to penetrate the body of the user when the injection needle penetrates the body of the user, said glucose sensor comprising an electrode wire wound around the injection needle in the form of a core, an insulating layer coated over the injection needle to insulate the injection needle from said electrode wire, and an enzyme member fitted around a portion of the injection needle adjacent to the injection tip while being insulated from the electrode wire, said enzyme member and said electrode wire penetrating the body of the user when the injection needle penetrates the body of the user, and leads connected to the enzyme member and the electrode wire, respectively, to electrically connect the enzyme member and the electrode wire to a voltage sensing means included in the automatic syringe device, the leads being buried in the depressing member and the feeding tube.

In accordance with another aspect, the present invention provides a portable automatic syringe device comprising a housing, a syringe separably received in the housing and contained with a liquid medicine, an injection needle unit coupled to the housing in such a fashion that it communicates with the syringe, the injection needle unit including a feeding tube, an "L" shaped injection needle member connected to one end of the feeding tube, a connector connected to the other end of the feeding tube, and a depressing member integrally formed with the injection needle member in such a fashion that the injection needle protrudes perpendicularly from the depressing member, the depressing member being depressed against the skin of a user upon penetrating the injection needle member into the subcutaneous tissue of the user, a piston slidably fitted in the syringe and separably received in the housing, the piston being vertically movable in the syringe to inject the liquid medicine into the injection needle unit, a vertical rotating shaft having a screw extending throughout the length thereof, push means threadedly coupled to the screw of the rotating shaft in such a fashion that it moves along the rotating shaft when the rotating shaft rotates, the push means being adapted to move the piston by the movement thereof, and power transmission means fixedly installed in the housing and adapted to transmit a drive force generated from a drive motor to the rotating shaft, further comprising: a glucose sensor attached to said injection needle and adapted to penetrate the body of the user when the injection needle penetrates the body of the user, said glucose sensor comprising an electrode wire wound around the injection needle in the form of a core, an insulating layer coated over the injection needle to insulate the injection needle from said electrode wire, and an enzyme member fitted around a portion of the. injection needle adjacent to the injection tip while being insulated from the electrode wire, said enzyme member and said electrode wire penetrating the body of the user when the injection needle penetrates the body of the user, and leads connected to the enzyme member and the electrode wire, respectively; voltage sensing means connected to the leads and adapted to sense a variation in resistance outputted from the glucose sensor; a control unit for comparing an output from said voltage sensing means with a reference value, thereby generating a control signal, said control unit comprising a microcomputer adapted to control the entire operation of said control unit; and a motor driving unit for controlling said drive motor in accordance with said control signal from said control unit, said motor driving unit comprising a relay controlled by the microcomputer, said drive motor controlled by an operation of said relay, and a gear mechanism adapted to select a desired output level of the drive motor under the control of the relay.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Figure 1:
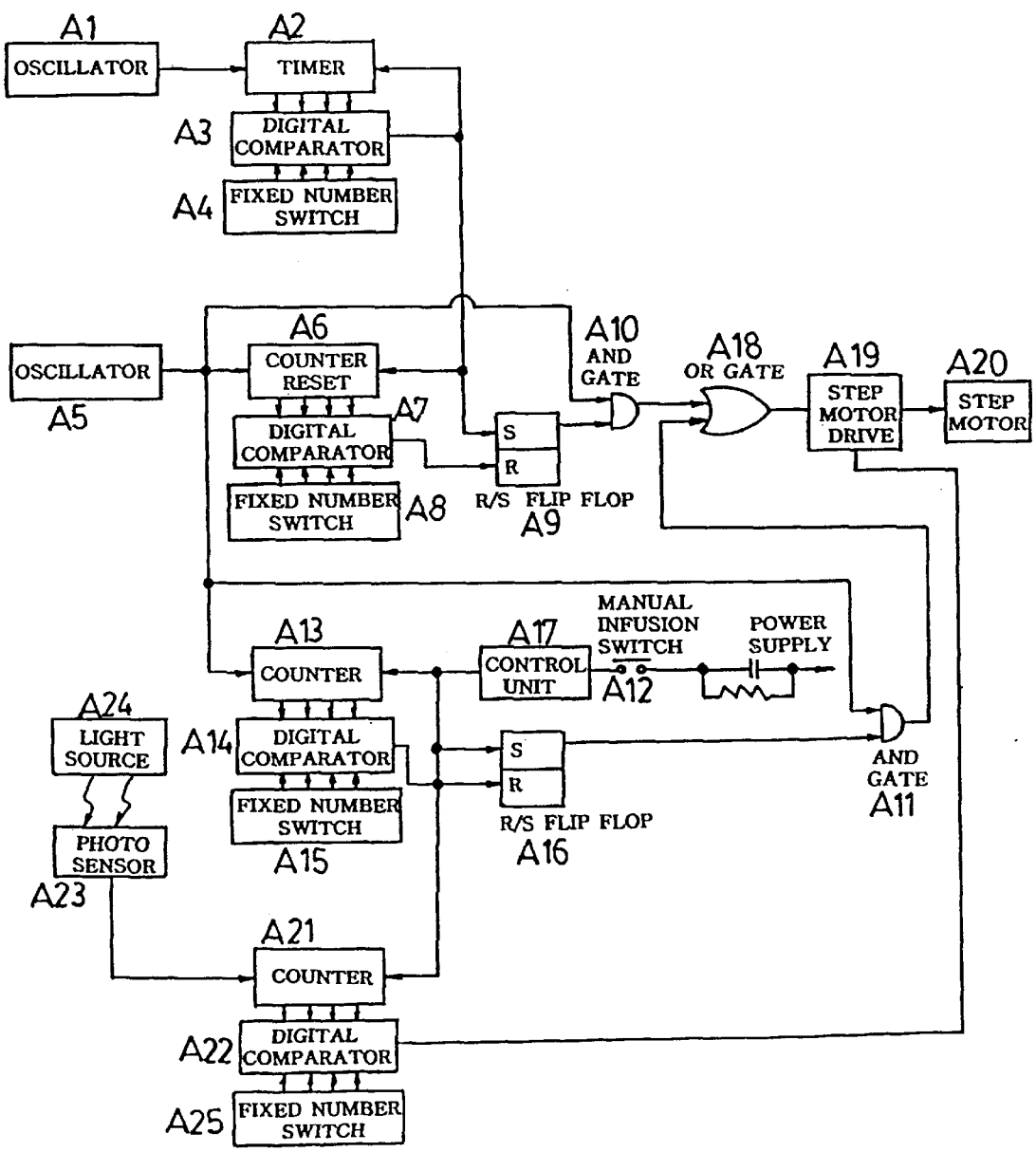
FIG. 1 is a block diagram illustrating a control circuit used in a conventional automatic syringe device.
Figure 2:
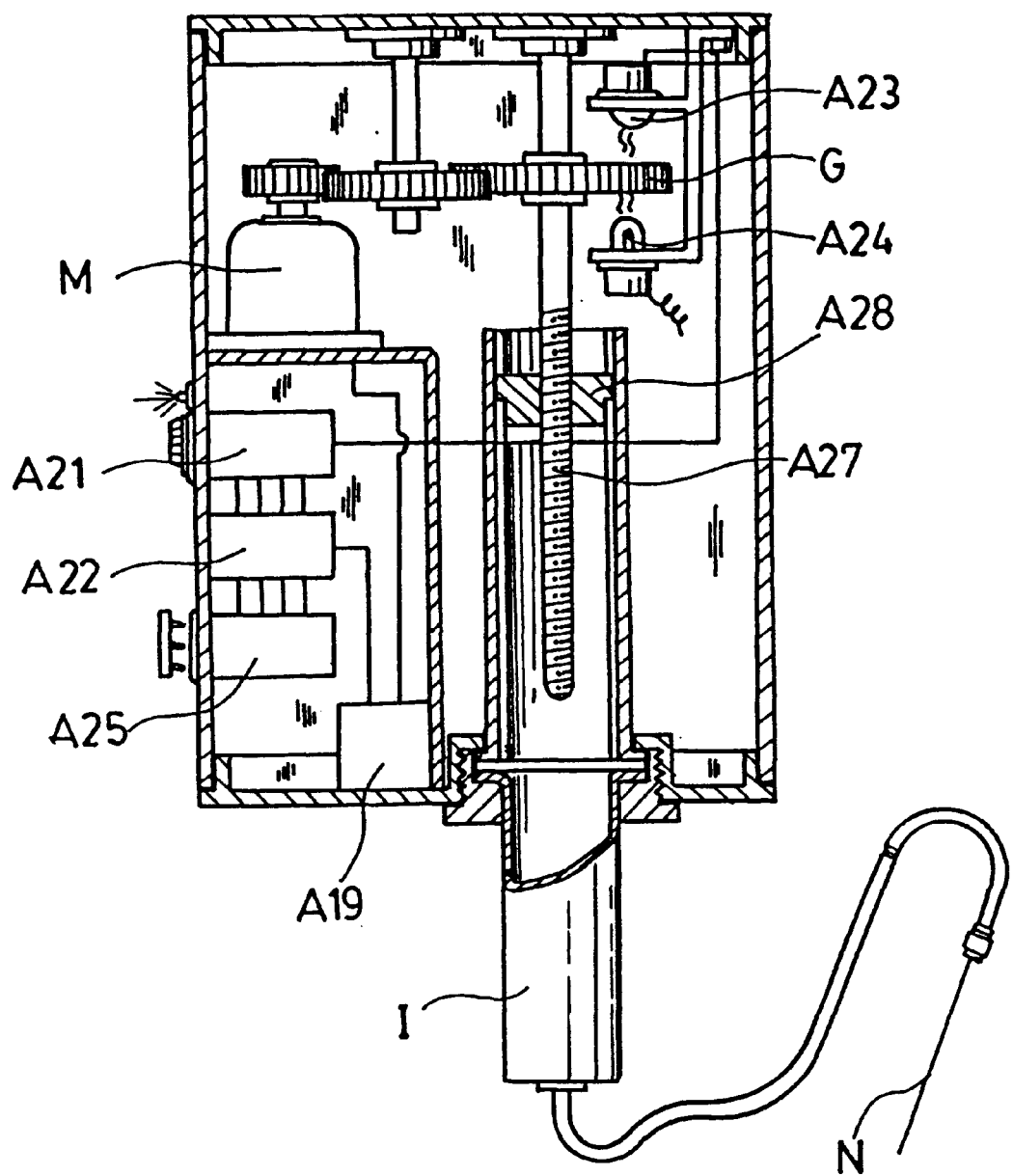
FIG. 2 is a cross-sectional view illustrating a structure of the automatic syringe device shown in FIG. 1.
Figure 3:
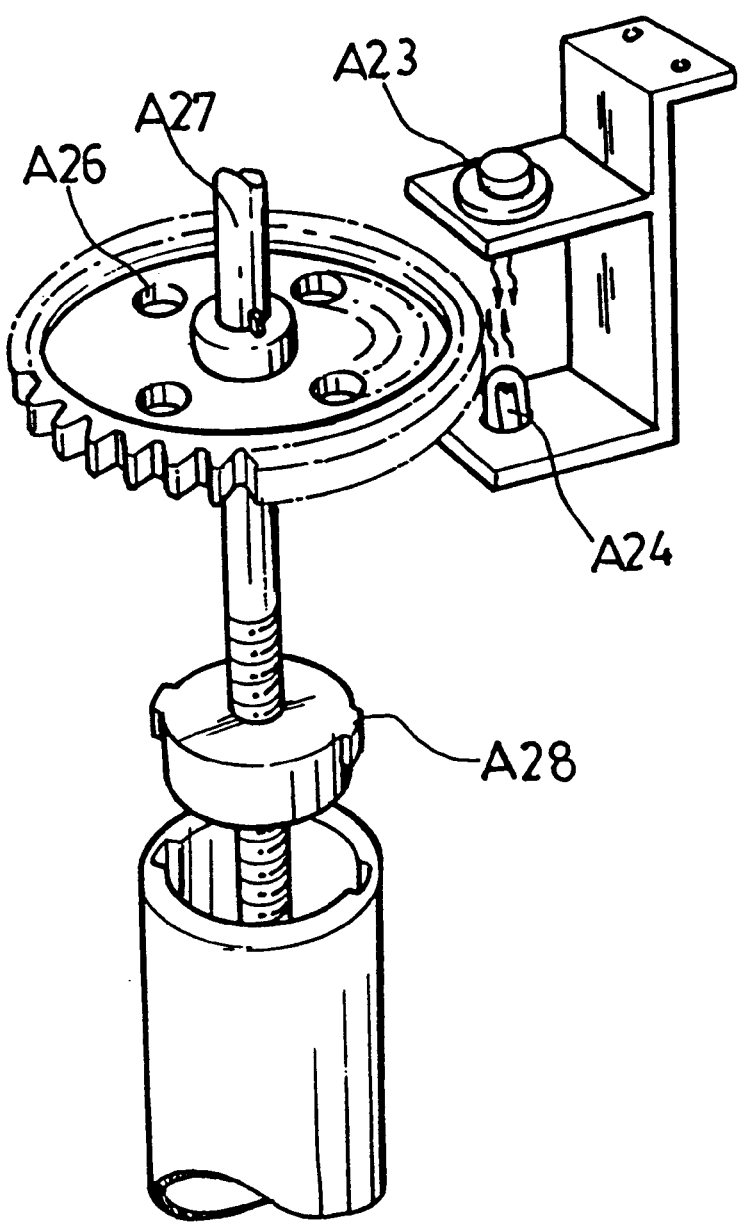
FIG. 3 is a perspective view illustrating the installation of a photo sensor in the automatic syringe device shown in FIG. 1.
Figure 4:
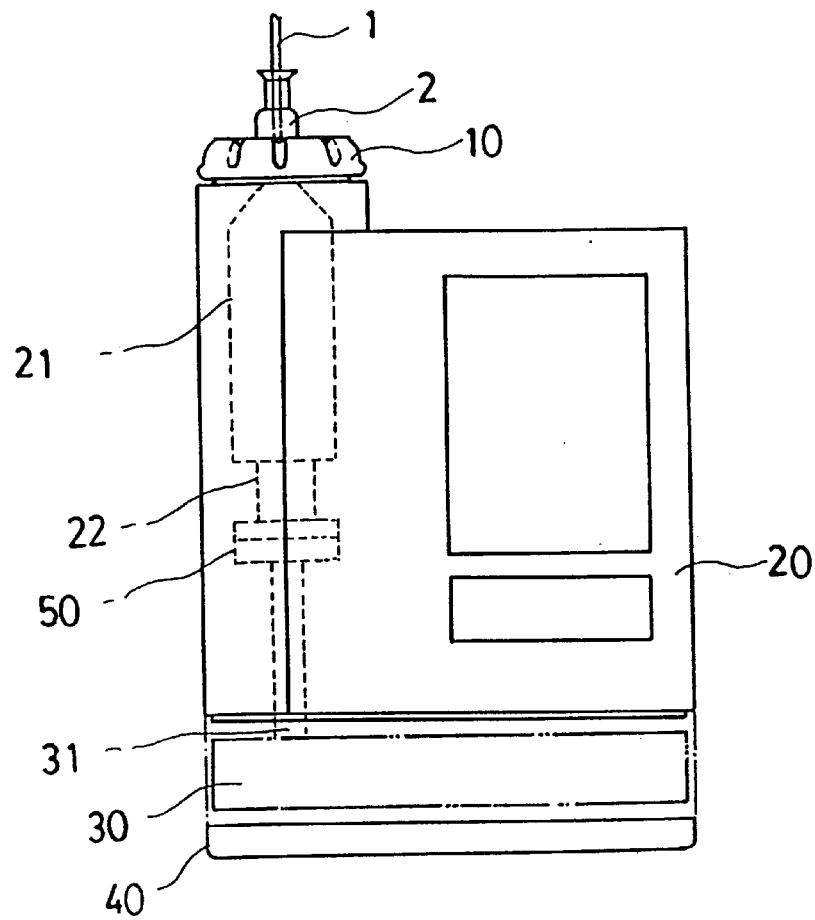
FIG. 4 is a front view illustrating another conventional automatic syringe device.
Figure 5:
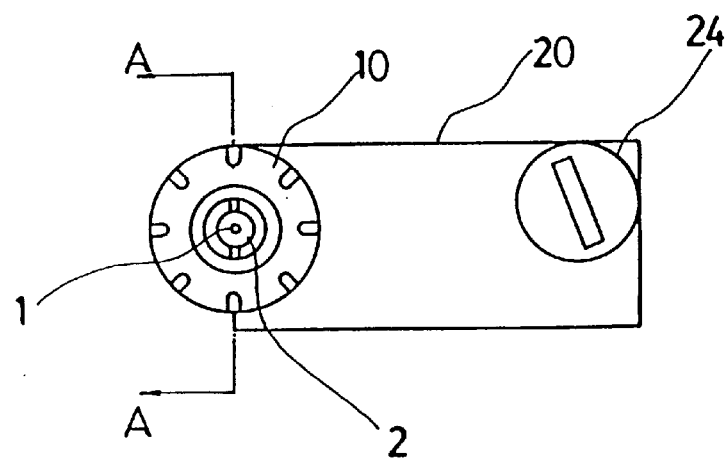
FIG. 5 is a plan view of FIG. 4.
Figure 6:
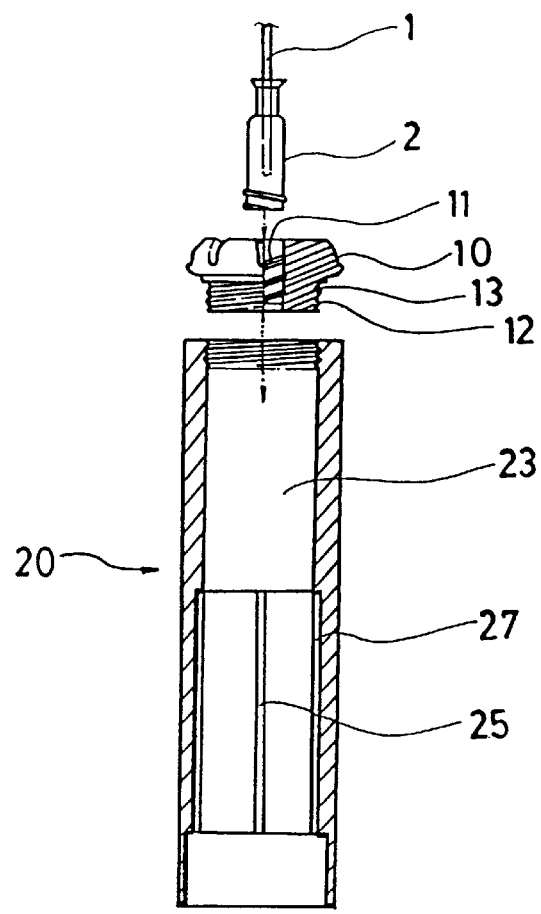
FIG. 6 is a cross-sectional view taken along the line A—A of FIG. 2.
Figure 7:
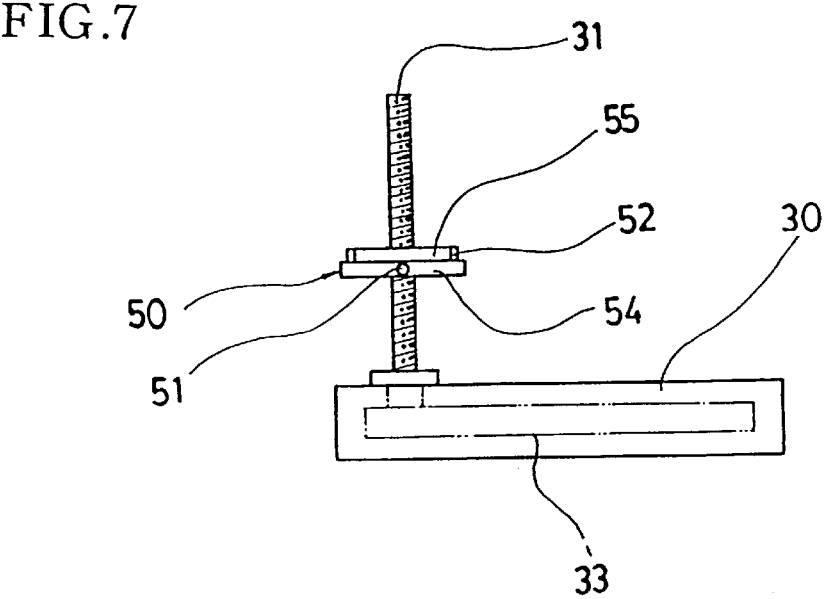
FIG. 7 is a view illustrating a conventional power transmission means.
Figure 8:
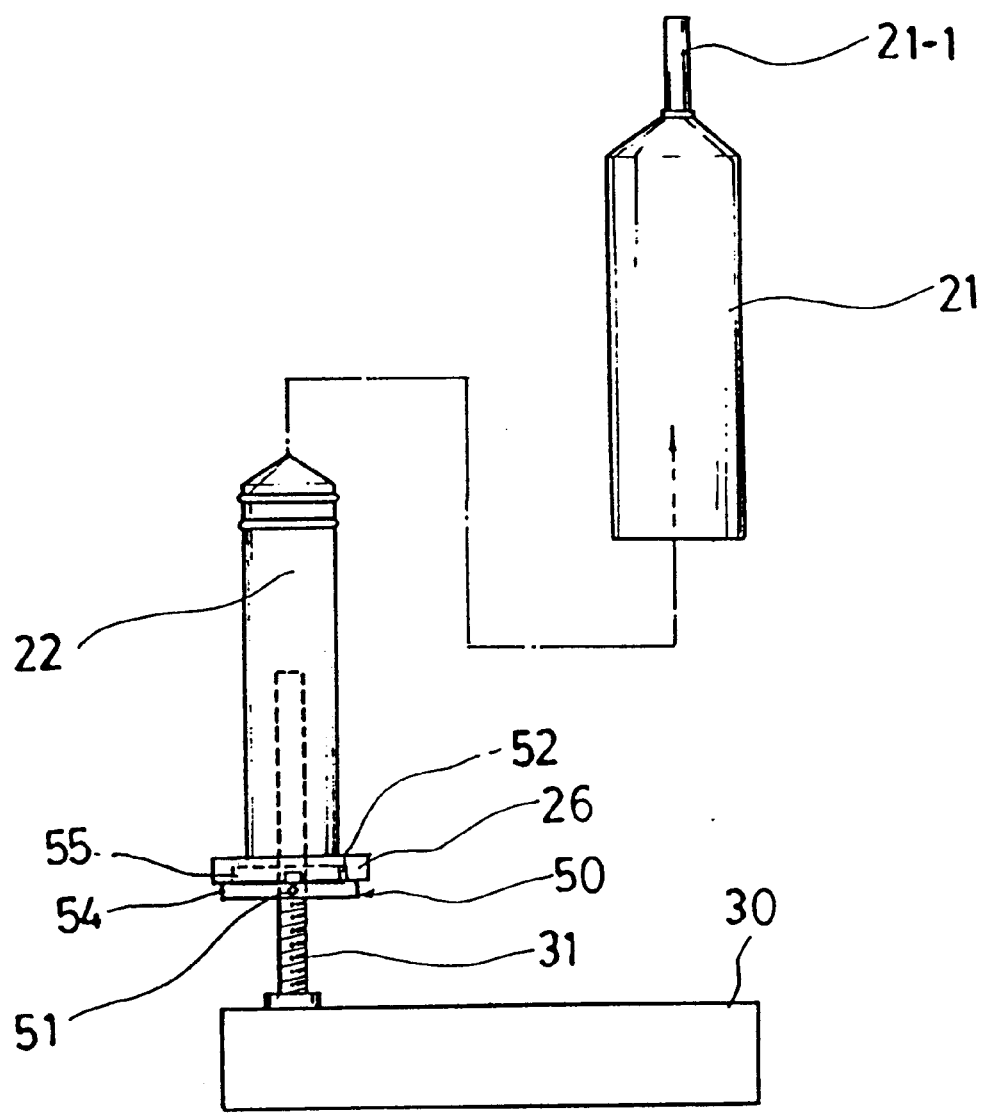
FIG. 8 is an exploded view illustrating a conventional push means.
Figure 9:
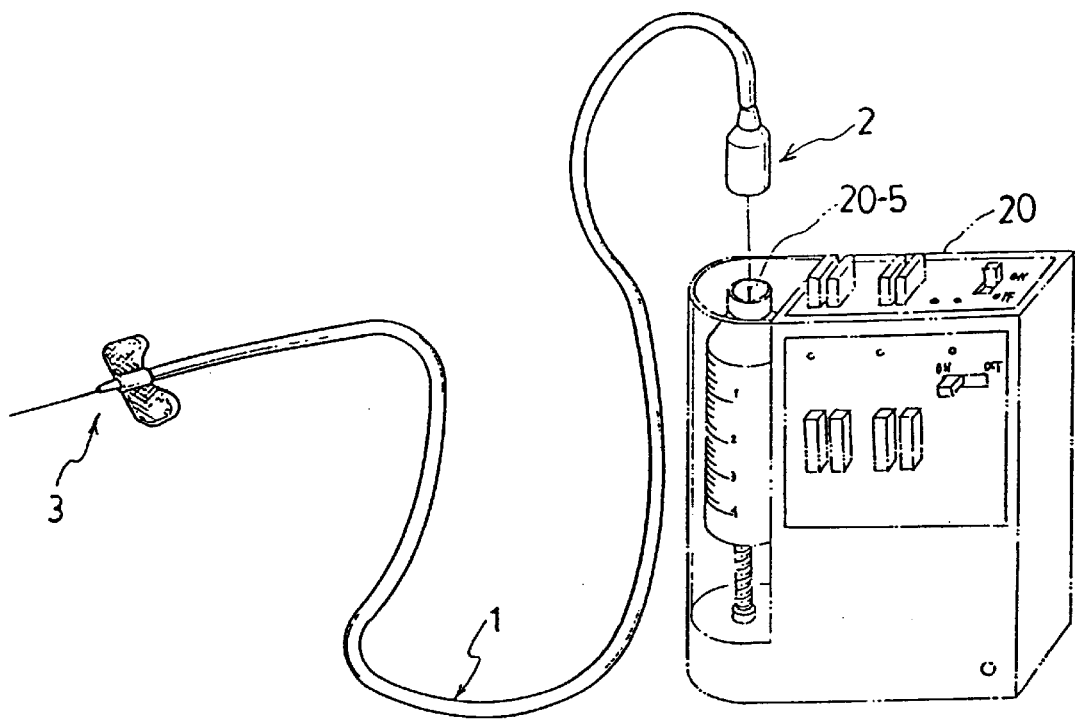
FIG. 9 is a perspective view illustrating an example of a conventional injection needle unit used for portable automatic syringe devices.
Figure 10:
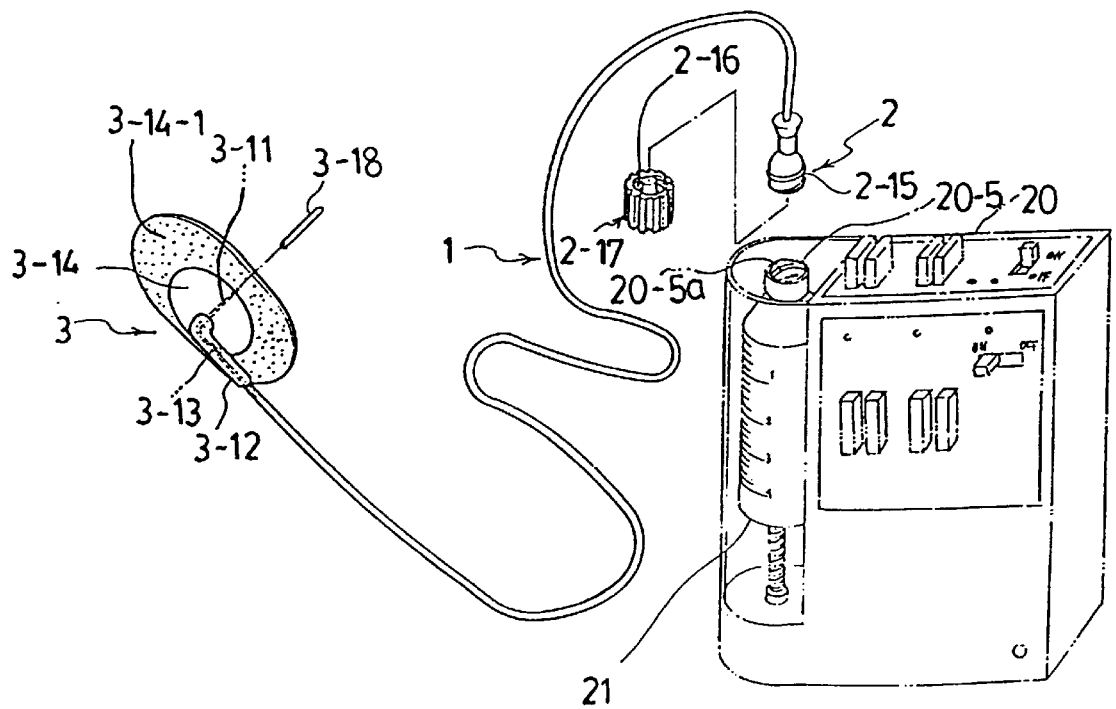
FIG. 10 is a perspective view illustrating another conventional injection needle unit.
Figure 11:
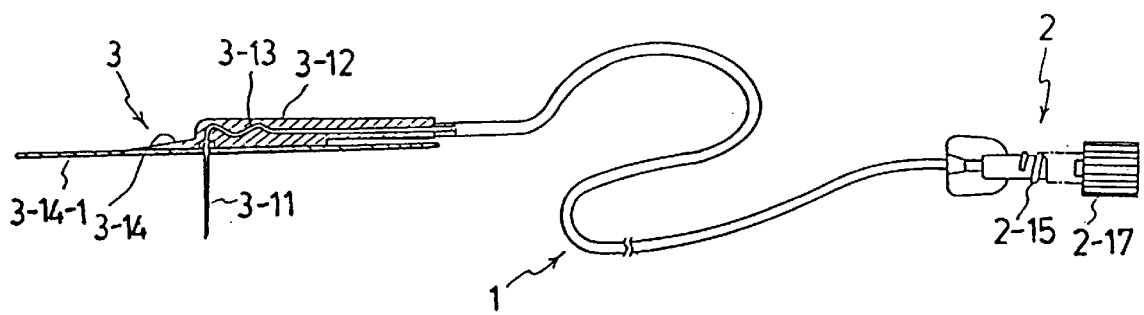
FIG. 11 is a partially-broken plan view illustrating the injection needle unit of FIG. 10.
Figure 12:
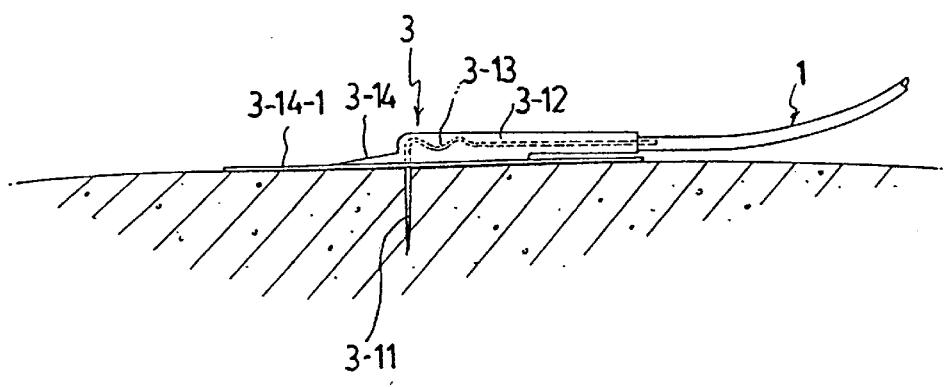
FIG. 12 is an enlarged view illustrating a using condition of the injection needle unit of FIG. 10.
Figure 13:
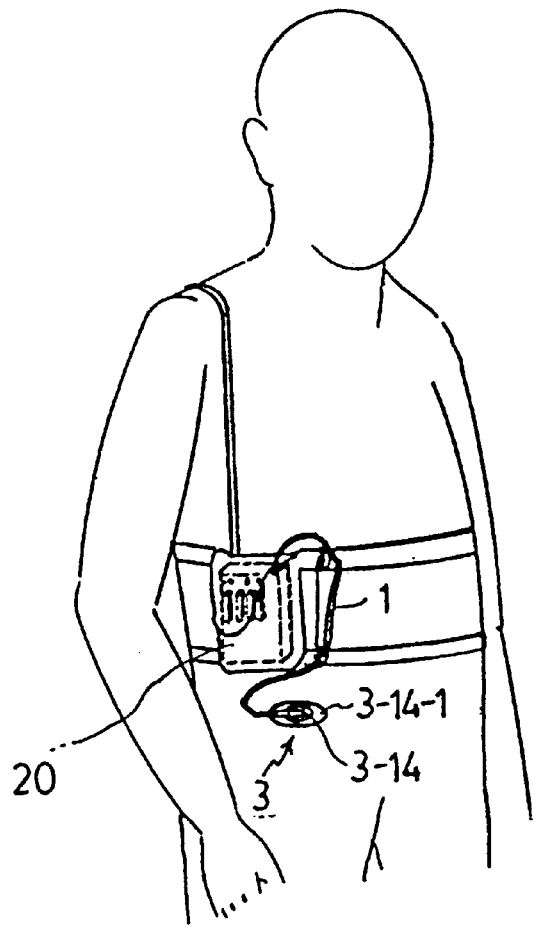
FIG. 13 is a perspective view illustrating a using condition of the injection needle unit of FIG. 10.
Figure 14:
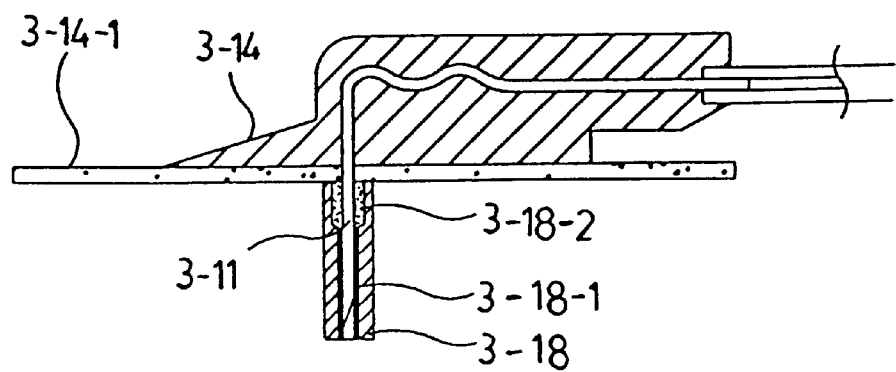
FIG. 14 is an enlarged view illustrating a part of the injection needle unit of FIG. 10.
Figure 15:
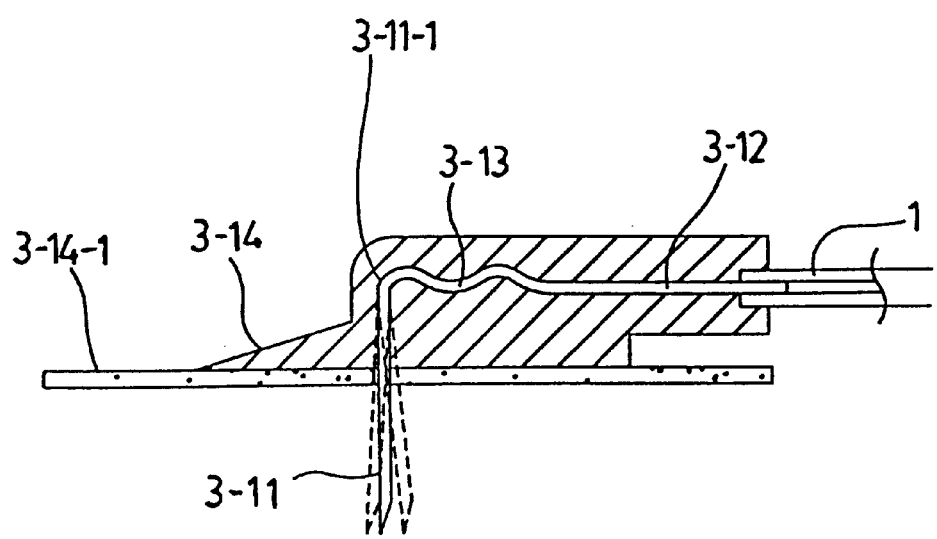
FIG. 15 is a view illustrating a drawback occurring when the injection needle unit of FIG. 10 is used.
Figure 16:
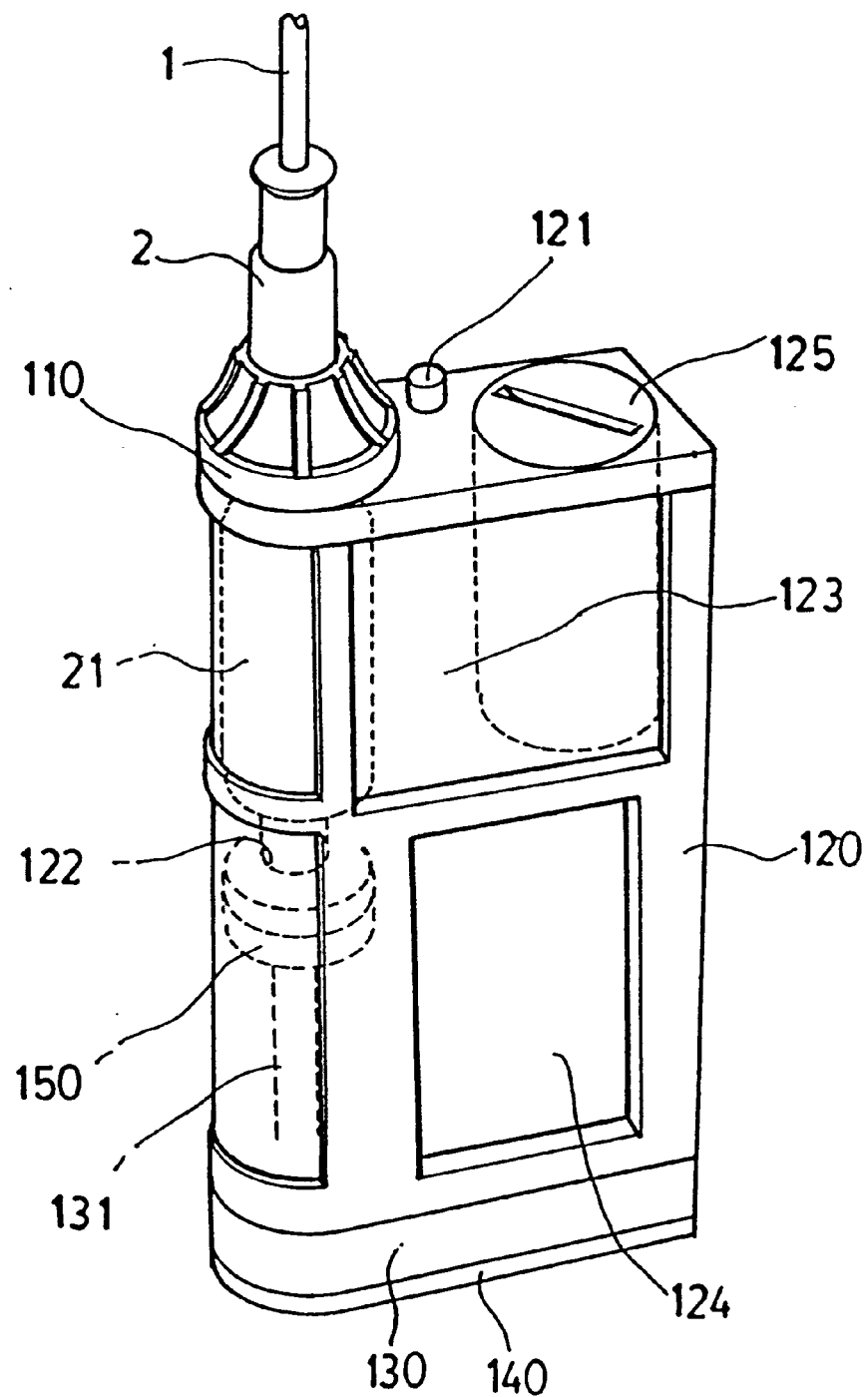
FIG. 16 is a perspective view illustrating a portable automatic syringe device according to an embodiment of the present invention.

First Type Portable Automatic Syringe Device Enabling Prolonged Injection of Liquid Medicine FIG. 16 is a perspective view illustrating a portable automatic syringe device according to an embodiment of the present invention. As shown in FIG. 16, the syringe device includes a housing 120, a syringe 21 separably received in the housing 120, a piston 122 slidably fitted in the syringe 21 and separably received in the housing 120, a piston push means 150 received in the housing 120 and adapted to vertically move the piston 122, a power transmission means 130 received in the housing 120 and adapted to generate a drive force, and a rotating shaft 131 received in the housing 120 and adapted to drive the piston push means 150 by the drive force transmitted from the power transmission means 130. The syringe device also includes an injection needle unit (in FIG. 16, only its feeding tube 1 and connector 2 are shown). The injection needle unit is connected to the housing 120 by means of a cover 110 which is sealably coupled to the upper end of the housing 120 at one side of the housing 120. A manipulation panel 123 is also installed on the housing 120. The manipulation panel 123 is electrically connected to a control circuit (not shown) installed in the housing 120 to control the power transmission means 130. A display 124 such as an LCD is also installed on the housing 120 in order to display the entire condition of the syringe device. At the other side of the housing 120, a battery cover 125 is separably coupled to the upper end of the housing 120 in order to carry a battery in the housing 120. A reset button 121 is also installed on the housing 120 to generate a reset signal for the control circuit. In FIG. 16, the reference numeral "140" is a bottom cover.

Figure 17:
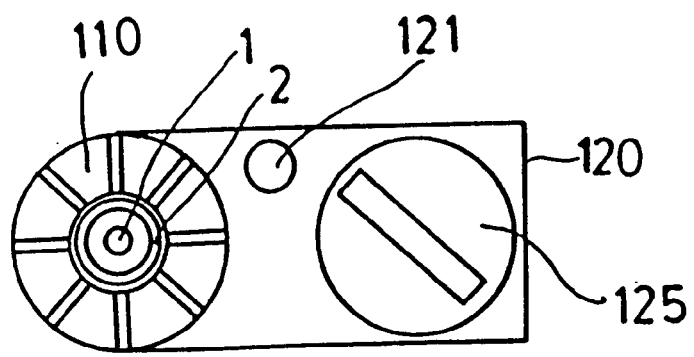
FIG. 17 is a plan view of FIG. 16.

Referring to FIG. 17, which is a plan view of FIG. 16, the cover 110 and battery cover 125 are arranged at opposite sides of the upper wall of the housing 120, respectively. The reset button 121 is arranged on the upper wall of the housing 120 between the covers 110 and 125.

Figure 18:
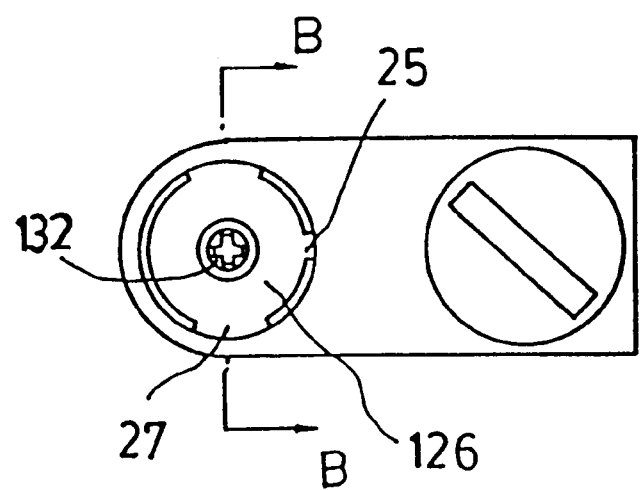
FIG. 18 is a plan view similar to FIG. 17, but eliminating a cover.
Figure 19:
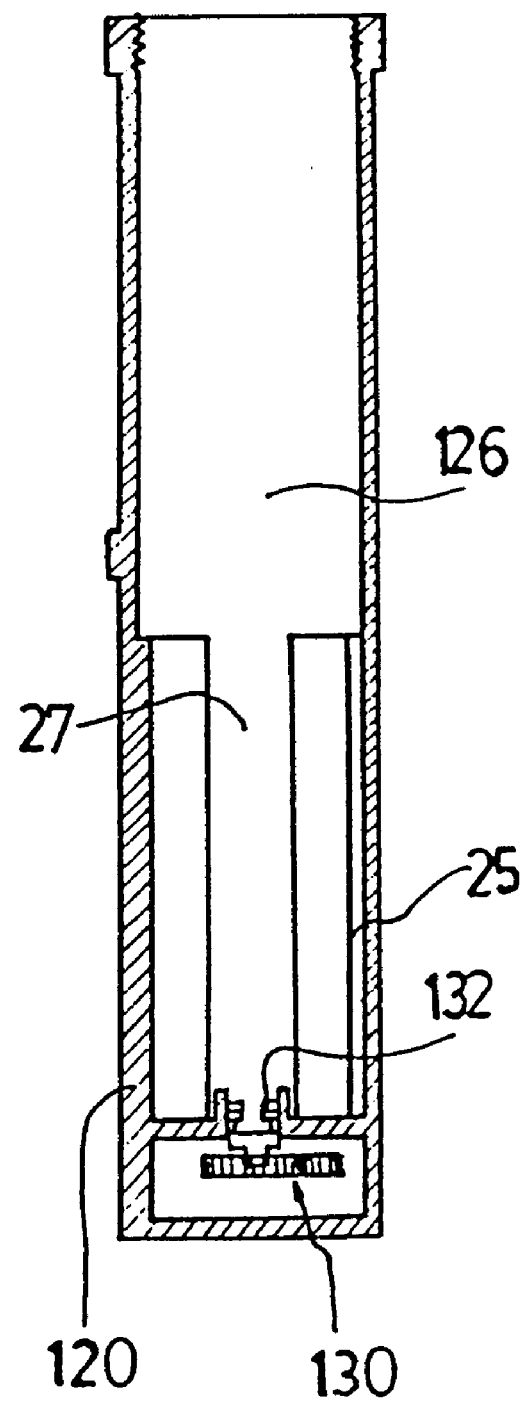
FIG. 19 is a cross-sectional view taken along the line B—B of FIG. 18.

FIG. 18 is a plan view similar to FIG. 17, but eliminating the cover 110. FIG. 18 illustrates the inner construction of the housing 120 in which the piston 122 and piston push means 150 are received. FIG. 19 is a cross-sectional view taken along the line B—B of FIG. 18. As shown in FIG. 19, the housing 120 has a syringe receiving chamber 126 defined in the interior of the housing 120. At the lower end of the syringe receiving chamber 126, the housing 120 has a hollow support portion in which a coupling member 132 coupled to the power transmission means 130 is rotatably fitted. The housing 120 is also formed, at its inner surface defining the syringe receiving chamber 126, with a vertical push means guide groove 25 adapted to guide a vertical movement of the push means 150 and vertical piston guide grooves 27 adapted to guide a vertical movement of the piston 122.

Figure 20:
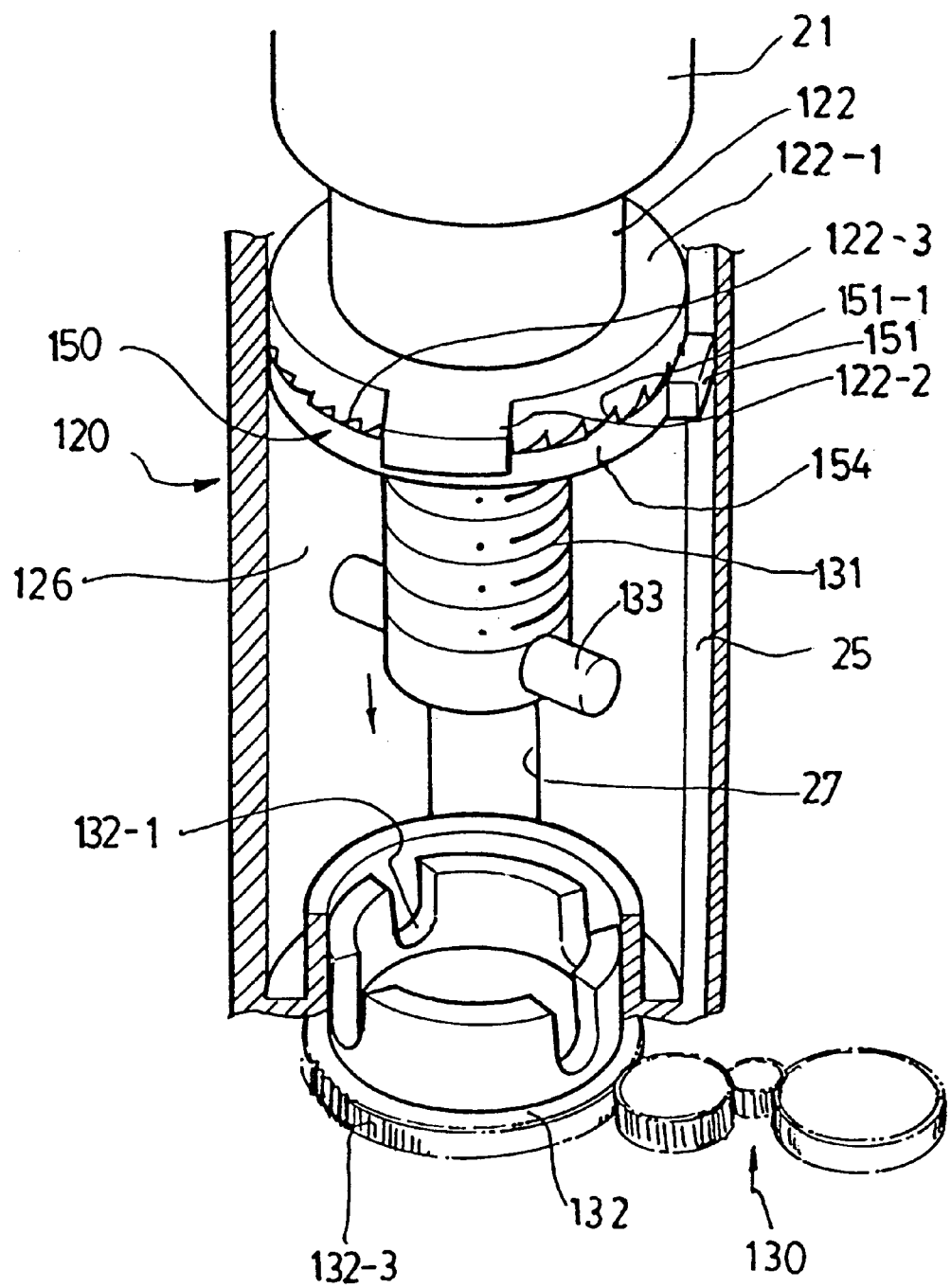
FIG. 20. is an enlarged perspective view illustrating a part of the automatic syringe device of FIG. 16.

FIG. 20 is an enlarged perspective view illustrating the configuration of the coupling member 132 to which the rotating shaft 131 is coupled. As mentioned above, the coupling member 132 is rotatably fitted in the hollow support portion of the housing 120 at the lower end of the syringe receiving chamber 126. As shown in FIG. 20, the coupling member 132 has a cross groove 132-1 in which a horizontal engaging pin 133 coupled to the lower end of the rotating shaft 131 is separably engaged. A gear 132-3 is also integrally formed with the coupling member 132. The gear 132-3 engages with an output gear of the power transmission means 130. Both ends of the engaging pin 133 are protruded from opposite sides of the lower end of the rotating shaft 131, respectively. By such a configuration, the coupling member 132 rotates by a drive force transmitted from the power transmission means 130 via the gear 132-3, thereby causing the rotating shaft 131 to rotate.

Figure 21:
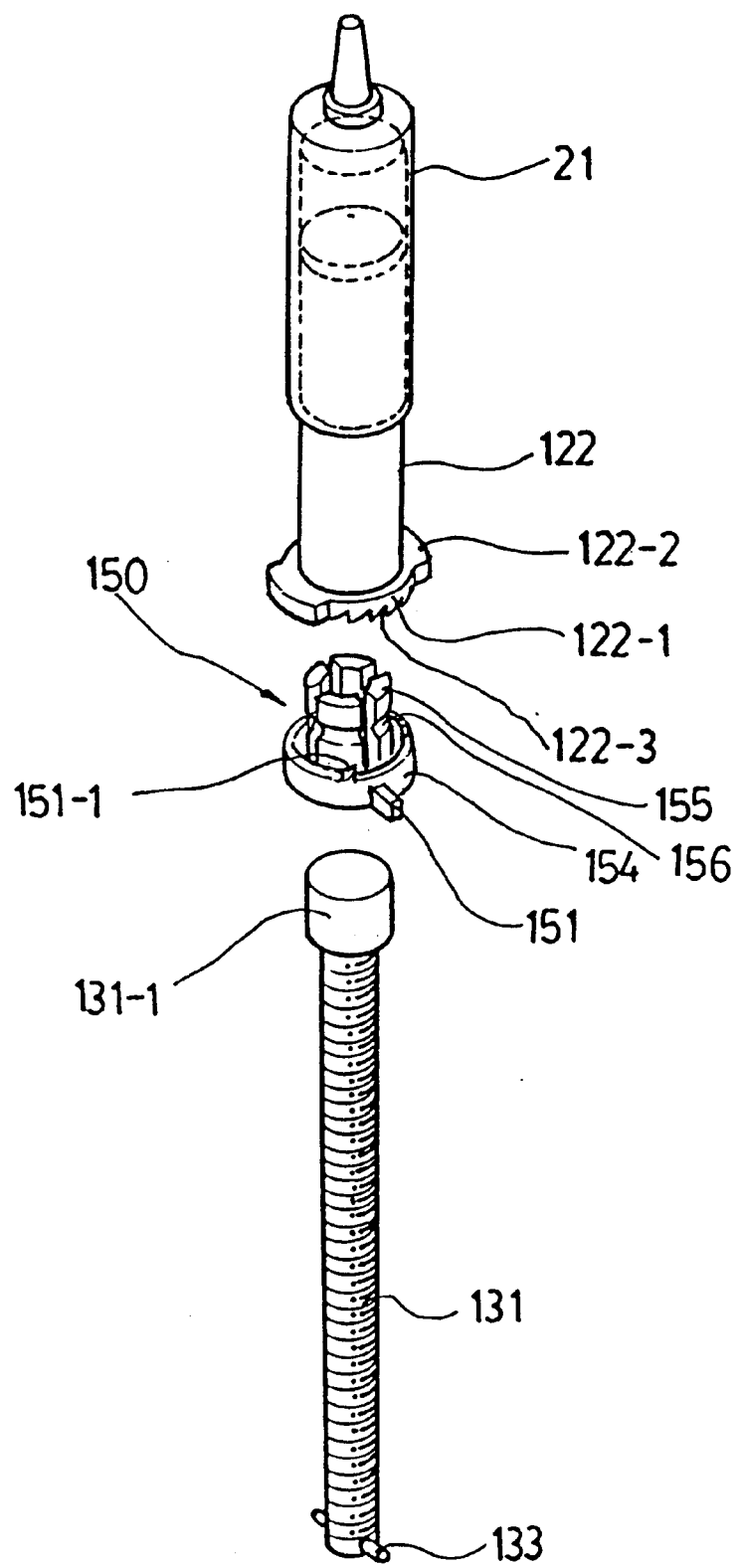
FIG. 21 is an enlarged perspective view illustrating a part of the automatic syringe device of FIG. 16.
Figure 22:
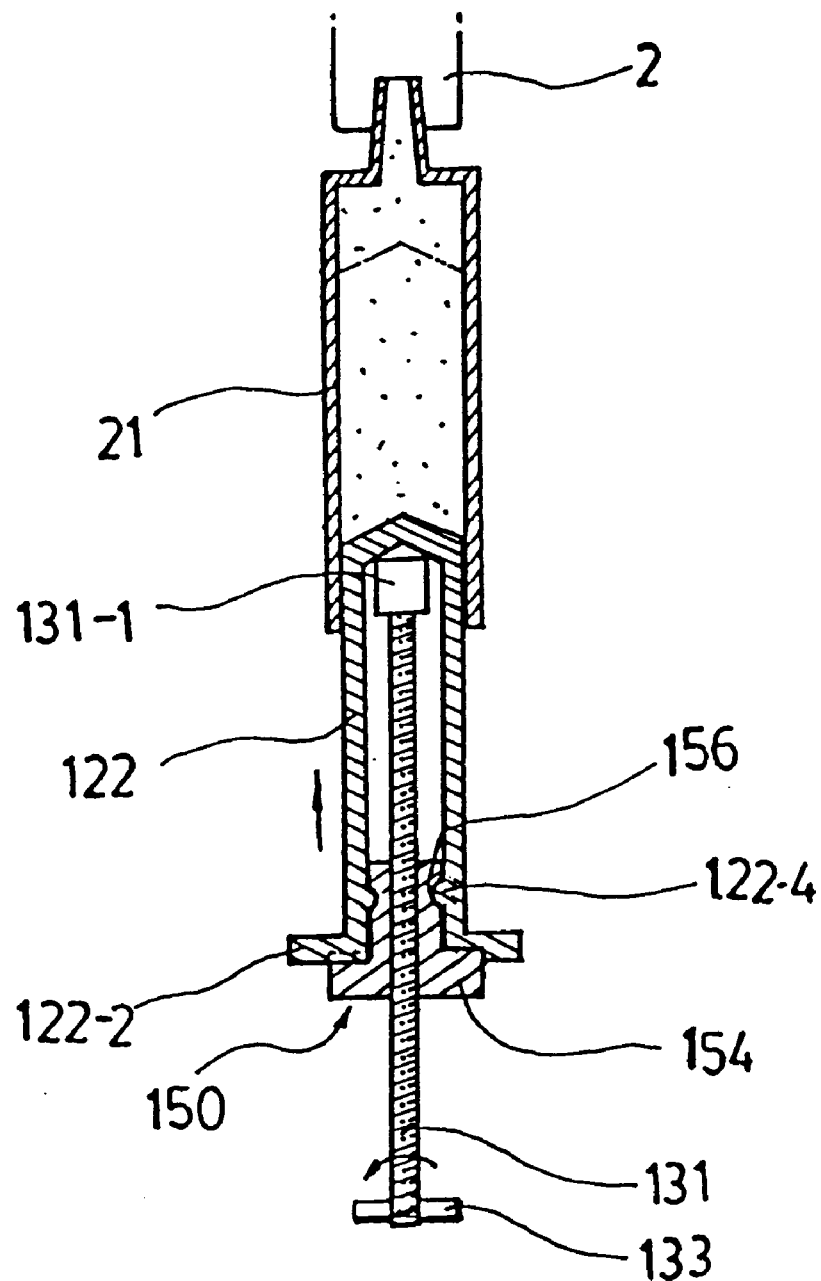
FIG. 22 is a cross-sectional view illustrating the coupled state of the elements of FIG. 21.

FIG. 21 is an exploded perspective view illustrating the rotating shaft 131, piston push means 150, piston 122, and syringe 21 separated from one another. FIG. 22 is a cross-sectional view illustrating the coupled state of the elements of FIG. 21. As shown in FIGS. 21 and 22, the rotating shaft 131 has a screw extending throughout the length thereof. A cap type head 131-1 is threadedly coupled to the upper end of the rotating shaft 131. The piston push means 150 is threadedly coupled to the rotating shaft 131 in such a fashion that it moves vertically along the rotating shaft 131. The piston push means 150 includes a push plate 154 threadedly coupled to the rotating shaft 131 in the form of a nut in such a fashion that it slides vertically along the rotating shaft 131. The push plate 154 is provided at its periphery with a radially-extending guide protrusion 151 engaged in the guide groove 25 of the housing 120 and adapted to guide the vertical movement of the push plate 154. The push plate 154 is also provided at its upper end with engaging protrusions 151-1. The piston push means 150 also includes a fitting member 155 extending upwardly from the push plate 154. The fitting member 155 is fitted into the lower end of the piston 122 which is open. An annular snap ring groove 156 is formed on the outer surface of the fitting member 155. The piston 122 has, at its lower portion, a snap ring 122-4 engaging with the snap ring groove 156. The piston 122 is also provided at its lower end with a radially-extending flange 122-1. A pair of radially-extending protrusions 122-2 are formed on the periphery of the flange 122-1. When the piston 122 is received in the syringe receiving chamber 126, the protrusions 122-2 engage with the guide grooves 27 of the housing 120, respectively, thereby guiding the vertical movement of the piston 122. A plurality of engaging grooves 122-3 are formed on the lower surface of the flange 122-1. When the piston push means 150 is fitted into the lower end of the piston 122, the engaging protrusions 151-1 thereof engage with optional ones of the engaging grooves 122-3 of the piston 122. In the illustrated case, the engaging grooves 122-3 have a small pitch to have the form of gear teeth whereas the protrusions 151-1 have a large pitch. In this case, it is possible to achieve an easy assembling process. In order to achieve an easier assembling process, the guide protrusions 122-2 of the piston 122 may be eliminated, thereby eliminating the reference position of the piston 122 upon assembling the piston 122. Of course, the provision of the guide protrusions 122-2 provides an advantage in that the piston 122 operates more accurately.

Figure 23:
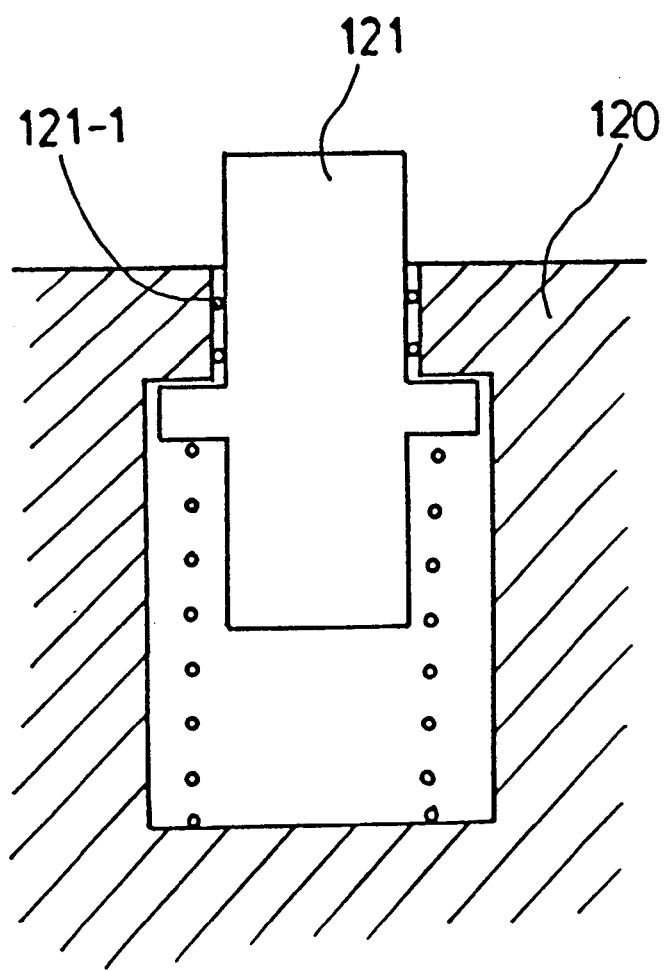
FIG. 23 is an enlarged cross-sectional view illustrating a reset button installed in accordance with the present invention.

FIG. 23 is a cross-sectional view illustrating the reset button 121 installed on the housing 120. The reset button 121 is slidably fitted in a hole defined in the upper wall of the housing 120 in such a manner that it is separated from the hole. The reset button 121 is upwardly biased by a compression coil spring so that its upper end is in a state protruded from the hole of the housing 120. At least one seal packing 121-1 is fitted around the reset button 121 to provide a sealing effect between the housing 120 and reset button 121.

Now, the syringe device having the above mentioned configuration according to the present invention will be described.

First, the pushplate 154 of the piston push means 150 is threadedly coupled to the rotating shaft 131 in such a manner that it is disposed at the middle portion of the rotating shaft 131. Thereafter, the engaging pin 133 is coupled to the lower end of the rotating shaft 131. Also, the cap type head 131-1 is threadedly coupled to the upper end of the rotating shaft 131. The rotating shaft 131 is then inserted into the lower end of the piston 122 until the fitting member 155 of the piston push means 150 is fitted in the lower end of the piston 122. In this state, the snap ring groove 156a of the fitting member 155 engages with the snap ring 122-4 of the piston 122. Also, the engaging protrusions 151-1 of the push plate 154 engage with optional ones of the engaging grooves 122-3 of the piston 122. The piston 122, which is coupled to the rotating shaft 131, is then fitted in the syringe 21 in such a manner that it is completely inserted into the syringe 21, as indicated by the double-dotted line in FIG. 22. In this state, a disposable injection needle (not shown) is fitted onto the tip of the syringe 21. Thereafter, the injection needle is penetrated into the interior of a phial through the plug of the phial. In this state, the piston 122 is pulled, along with the rotating shaft 131, to suck a liquid medicine contained in the phial into the syringe 21, as indicated by the solid line in FIG. 22. In order to allow the engaging pin 133 of the rotating shaft 131 to be accurately engaged in the cross groove 132-1 of the coupling member 132 when the syringe 21 filled with the liquid medicine is inserted into the syringe receiving chamber 126 of the housing 120, it is necessary to appropriately adjust an initial length of the rotating shaft 131 protruded from the piston 122 in accordance with the amount of the liquid medicine contained in the syringe 21. In order to achieve an easy and convenient adjustment of the initial protruded length of the rotating shaft 131, a scale (not shown) may be formed on the housing 120. Alternatively, a mark (not shown) indicative of a reference position for the rotating shaft 131 may be formed on the housing 120. Otherwise, a length measuring jig may be used. In this state, the syringe 21, in which the piston 122 is fitted, is inserted into the syringe receiving chamber 126 of the housing 120 in such a manner that the engaging pin 133 of the rotating shaft 131 is engaged in the cross groove 132-1 of the coupling member 132, as indicated by the arrow in FIG. 20. Thereafter, the cover 110 is threadedly coupled to the upper end of the housing 120, so that the injection needle unit is coupled to the syringe tip 21-1 of the syringe 21.

When the motor (not shown) drives under the above condition, its drive force is transmitted to the gear 132-3 via the power transmission means 130. Accordingly, the coupling member 132 integral with the gear 132-3 rotates. The rotation of the coupling member 132 results in a rotation of the rotating shaft 131 because the engaging pin 133 of the rotating shaft 131 is engaged in the cross groove 132-1 of the coupling member 132. The rotation of the rotating shaft 131 is carried out in a speed-reduced manner because the drive force of the motor is transmitted via the power transmission means 130. When the rotating shaft 131 rotates, the push means 50 moves vertically because the guide protrusion 151 of the push plate 154 is engaged in the guide groove 25 of the housing 120. For example, when the rotating shaft 131 rotates counter-clockwise, as shown in FIG. 22, the push plate 154 moves upwardly while being guided by the guide groove 25. As a result, the piston 122 coupled to the push plate 154 moves upwardly. Accordingly, the liquid medicine contained in the syringe 21 is injected into the body of the user, into which the injection needle of the injection needle unit through the connector 2 penetrates, via the connector 2 and feeding tube 1. As the injection of the liquid medicine is carried out for a prolonged time, the piston 122 reaches its initial position indicated by the double-dotted line -in FIG. 22. In this state, the user separates the injection needle unit from the body and completes the use of the syringe device. Thereafter, the connector 2 of the injection needle unit is separated from the cover 110 which is, in turn, released from the housing 120. The syringe 21, piston 122, push means 150 and rotating shaft 131 assembled together are removed from the syringe receiving chamber 126 of the housing 120. Where it is desired to use again the syringe device, a liquid medicine is filled in the syringe 21 in accordance with the above mentioned piston function. Thereafter, the user rotates the rotating shaft 131 by hand so that the rotating shaft 131 is inserted into the piston 122 to its original position. That is, the rotating shaft 131 is adjusted to have a desired initial length protruded from the piston 122. In order to achieve an easy adjustment of the initial protruded length of the rotating shaft 131, it may be possible to use a scale formed on the housing 120, a mark indicative of a reference position for the rotating shaft 131 formed on the housing 120, or a length measuring jig As mentioned above, the reason why the rotating shaft 131 is adjusted to have a desired initial length protruded from the piston 122 is to allow the engaging pin 133 of the rotating shaft 131 to be accurately engaged in the cross groove 132-1 of the coupling member 132 when the syringe 21 is fitted in the syringe receiving chamber 126 of the housing 120.

Once the push plate 154 is threadedly coupled to the rotating shaft 131, it is prevented from being separated from the rotating shaft 131 because the cap type head 131-1 is threadedly coupled to the upper end of the rotating shaft 131. Accordingly, an improvement in durability is obtained.

Where the injection of the liquid medicine contained in the syringe 21 is achieved by an upward movement of the piston 122 resulting from an upward movement of the push means 150 along the rotating shaft 131, it is necessary to return the upwardly-moved push means 150 to its initial position after filling again the syringe 21 with a liquid medicine to inject again the liquid medicine. However, it is disadvantageous to return the push means 150 to its initial position by reversely rotating the rotating shaft 131 using a drive force from the motor. This is because the drive force from the motor is transmitted to the rotating shaft 131 in a speed-reduced manner, so that a lengthened time of about 5 to 10 minutes is taken for the push means to return to its initial position. In this case, accordingly, there is a wastage of time. In order to solve this disadvantage, in accordance with the illustrated embodiment of the present invention, the rotating shaft 131 is configured to be separable from the motor so that it is manually rotated. Accordingly, it is possible to easily adjust the initial position of the push means by a manual rotation of the rotating shaft 131. The rotating shaft 131 is also configured to be rotated only in one direction by a drive force from the motor. Accordingly, the control for the motor is simplified. This results in a reduction in the manufacturing costs.

In particular, all the cover 110, battery cover 125, reset button 121 and bottom cover 140 are sealably configured in accordance with the illustrated embodiment of the present invention, even though such a configuration is omitted from the drawings because it is well known. In this case, a vacuum is generated in the interior of the housing 120 as the liquid medicine contained in the syringe 21 is injected into the body of the user. As a result, the piston 122 is overloaded. This problem may be eliminated by forming the reset button 121 using a well-known semi-permeable material preventing penetration of moisture while allowing ventilation of air. In this case, it is possible to prevent a vacuum from being generated in the interior of the housing 120 while still maintaining a moisture sealing effect between the housing 120 and reset button 121. An increase in the manufacturing costs occurs when the entire portion of the housing 120 is made of the semi-permeable material. However, where a small part of the housing 120, f or example , the reset button 121, is made of the semi-permeable material, it is possible to minimize an increase in th e manufacturing costs while maintaining a permeable effect for the housing 120 and providing convenience in installation. In this case, preferably, at least one seal packing 121-1 is fitted around the reset button 121 to provide a desired sealing effect between the housing 120 and reset button 121.

First Type Injection Needle Unit

Figure 24:
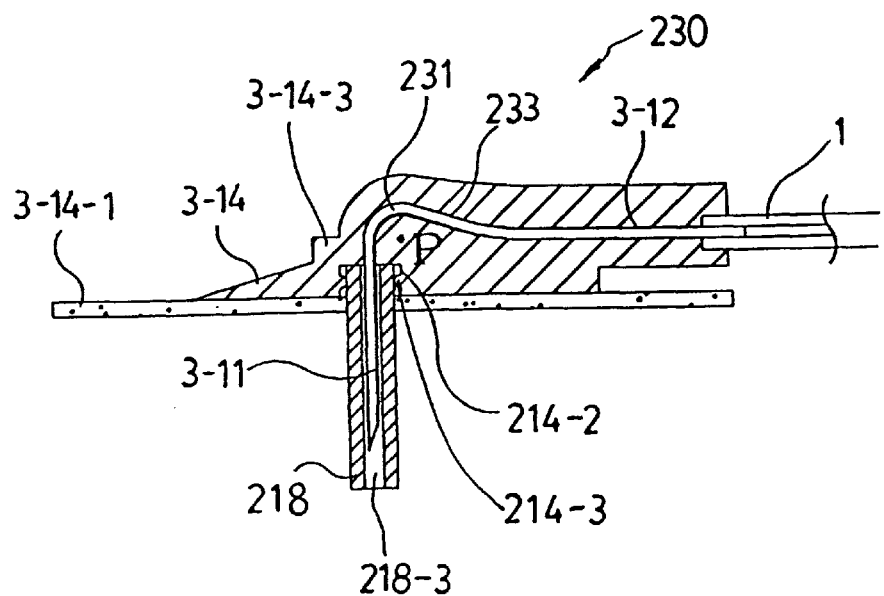
FIG. 24 is a cross-sectional view illustrating an injection needle unit according to an embodiment of the present invention.

FIG. 24 is a cross-sectional view illustrating an injection needle unit according to an embodiment of the present invention. As shown in FIG. 24, the injection needle unit includes a feeding tube 1, an "L" shaped injection needle member 230 connected to one end of the feeding tube 1, and a connector 2 connected to the other end of the feeding tube 1.

The injection needle member 230 has an "L" shaped structure including a vertical portion, namely, an injection needle 3-11 provided with a needle tip, and a horizontal portion, namely, a connecting rib 3-12 fitted in one end of the feeding tube 1. The injection needle member 230 also has a curved portion 231 which preferably has a quadrant shape extending circumferentially about a center P, flush with the upper end of the injection needle 3-11, between the injection needle 3-11 and the connecting rib 3-12. The curved portion 231 of the injection needle member 230 has a downward slant portion 233 so that it is smoothly connected to the connecting rib 3-12.

The injection needle unit also includes a depressing member 3-14 integrally formed with the injection needle member 230 in such a fashion that the injection needle 3-11 protrudes perpendicularly from the depressing member 3-14. The depressing member 3-14 is depressed against the skin of the user upon penetrating the injection needle member 230 into the subcutaneous tissue. The depressing member 3-14 is provided with a protection cap groove 214-2 for partially receiving a tube-shaped protection cap 218 adapted to protect the injection needle 3-11 of the injection needle member 230. The protection cap 218 has a through hole 218-3 for receiving the injection needle 3-11 of the injection needle member 230. The through hole 218-3 has a diameter larger than that of the injection needle 3-11. In order to firmly hold the protection cap 218, the protection cap groove 214-2 is provided at its surface with an annular protrusion 214-3. A bacterial infection prevention member 3-14-1, which is made of a disinfected nonwoven fabric, is attached to the surface of the depressing member 3-14 which comes into contact with the skin of the user upon penetrating the injection needle unit 230 into the subcutaneous tissue.

Figure 25:
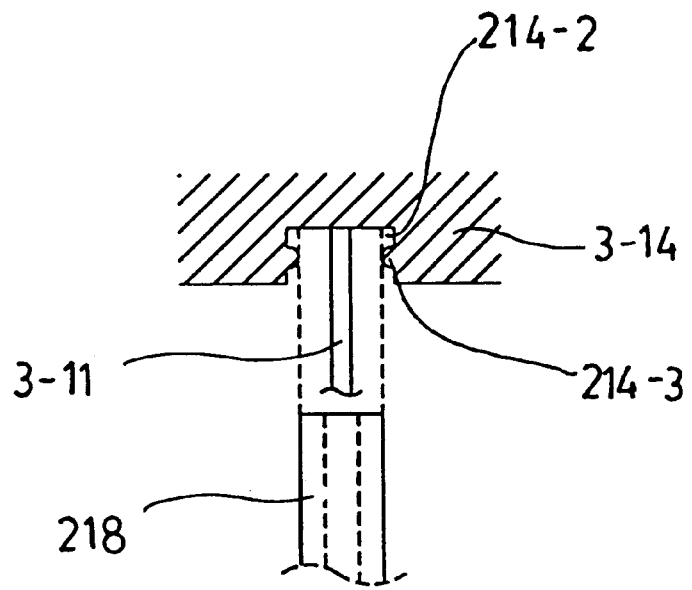
FIG. 25 is an enlarged cross-sectional view illustrating a part of the injection needle unit shown in FIG. 24.
Figure 26:
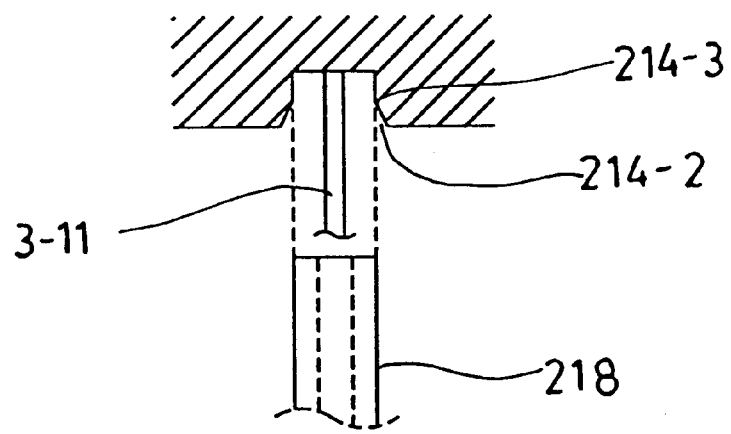
FIG. 26 is a view similar to FIG. 25, but illustrating a configuration different from that of FIG. 25.

As shown in FIGS. 25 and 26, the protection cap 218 is firmly fitted at its upper end in the protection cap groove 214-2 of the depressing member 3-14 while receiving the injection needle 3-11 of the injection needle member 230 in its through hole 218-3. Since the through hole 218-3 has a diameter larger than that of the injection needle 3-11, it is possible to easily fit the injection needle 3-11 in the protection cap 218. Since the protection cap groove 214-2 has the annular protrusion 214-3, the protection cap 218 is firmly held by the protection cap groove 214-2. In the injection needle unit according to the illustrated embodiment, there is no capillarity phenomenon occurring between the inner surface of the needle protection cap 218 and the outer surface of the injection needle 3-11 when a liquid medicine (insulin) contained in a syringe is outwardly discharged from the injection needle 3-11 to vent air existing in the feeding tube 1 and injection needle 3-11 prior to an injection of the liquid medicine into the body of the user. This is because the through hole 218-3 has a diameter larger than that of the injection needle 3-11. Accordingly, there is no phenomenon that a part of the discharged liquid medicine is absorbed in the bacterial infection prevention member 3-14-1.

Where it is desired to inject insulin contained in the automatic insulin syringe device using the above mentioned injection needle unit, the user pulls the protection cap 218 by one hand while holding the depressing member 3-14 by the other hand, thereby causing the protection cap 218 to be removed from the injection needle 3-11. The user then penetrates the injection needle 3-11 into the subcutaneous tissue while depressing the depressing member 3-14 against the skin (in particular, the skin of the abdomen) by fingers. The user may move excessively during injection. In this case, the injection needle 3-11 moves with respect to the depressing member 3-14. Such a movement of the injection needle 3-11 may also occur where the user straightens the injection needle 311 when the injection needle 3-11 is carelessly bent prior to the use thereof. In the case of the above mentioned injection needle unit, even when the injection needle 3-11 moves as mentioned above, it is possible to prevent the injection needle 3-11 from being damaged (broken) because the curved portion 231 of the injection needle member 230 provides a flexibility capable of absorbing stress applied to the injection needle 3-11. In particular, since the curved portion 231 of the injection needle member 230 is smoothly connected to the connecting rib 3-12 by the downward slant portion 233 even though it is positioned at a level higher than the connecting rib 3-12, the injection needle 3-11 is smoothly connected to the connecting rib 3-12 in a curved manner. Accordingly, there is no possibility of a breakage of the injection needle member 230 even when the injection needle 3-11 is subjected to impact.

Figure 27:
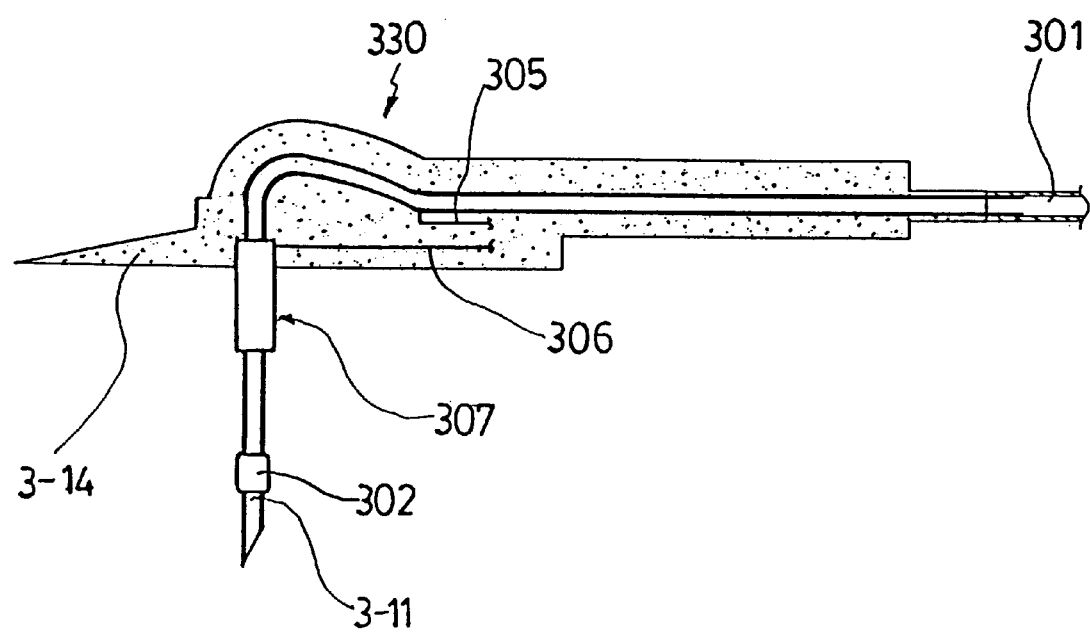
FIG. 27 is a cross-sectional view partially illustrating an injection needle unit according to another embodiment of the present invention.
Figure 28:
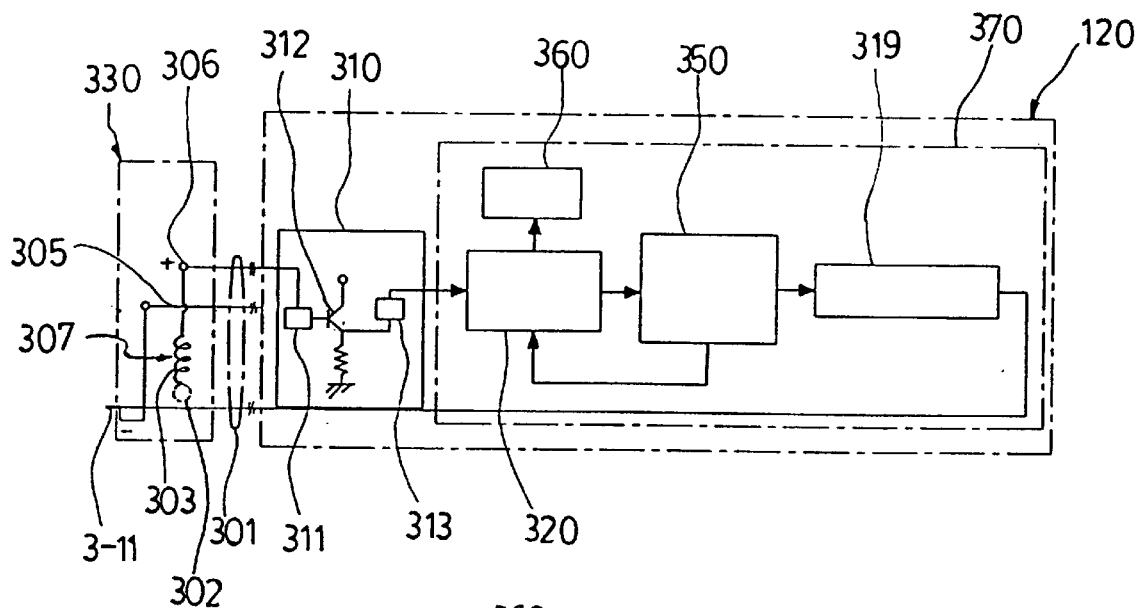
FIG. 28 is a block diagram illustrating an automatic syringe device using the injection needle unit of FIG. 27 in accordance with the present invention.
Figure 29:
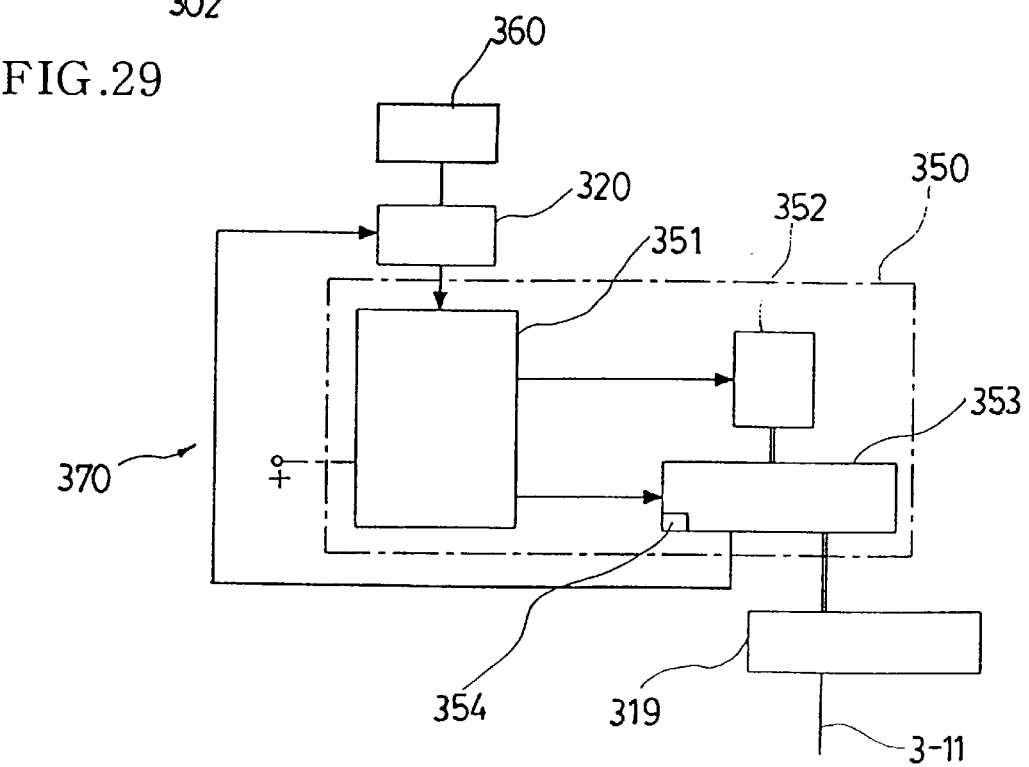
FIG. 29 is a block diagram illustrating a motor driving unit included in the automatic syringe device of FIG. 28 in accordance with the present invention.
Figure 30:
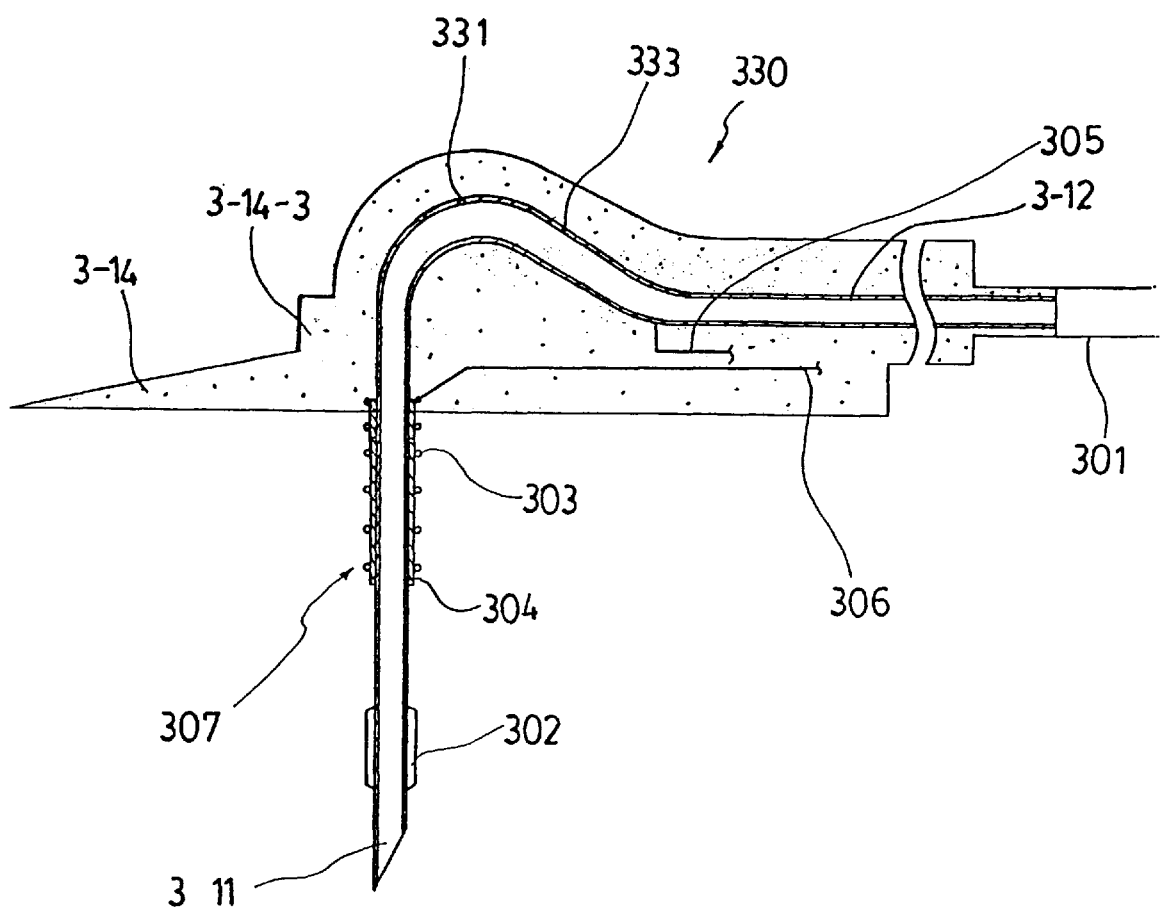
FIG. 30 is an enlarged view-of FIG. 27.

Second Type Injection Needle Unit and Second Type Portable Automatic Syringe Device FIG. 27 is a cross-sectional view partially illustrating an injection needle unit according to another embodiment of the present invention. FIG. 28 is a block diagram illustrating an automatic syringe device using the injection needle unit of FIG. 27 in accordance with the present invention. FIG. 29 is a block diagram illustrating a motor driving unit included in the automatic syringe device of FIG. 28 in accordance with the present invention. In addition, FIG. 30 is an enlarged view of FIG. 27.

As shown in FIG. 27, the injection needle unit includes a feeding tube 301, and an "L" shaped injection needle member 330 connected to one end of the feeding tube 301. Although not shown, a connector is connected to the other end of the feeding tube 301 in order to connect the injection needle unit to the housing of an automatic syringe device. The injection needle member 330 has an "L" shaped structure including an injection needle 3-11 provided with a needle tip, and a connecting rib 3-12 fitted in one end of the feeding tube 301. The injection needle member 330 also has a curved portion 331 formed between the injection needle 3-11 and the connecting rib 3-12 while having a shape similar to the curved portion 231 of FIG. 24. The curved portion 331 of the injection needle member 230 has a downward slant portion 333 so that it is smoothly connected to the connecting rib 3-12. A depressing member 3-14 is integrally formed with the injection needle member 330 in such a fashion that the injection needle 3-11 protrudes perpendicularly from the depressing member 3-14. The above mentioned configurations of the injection needle unit are the same as those shown in FIG. 24.

The injection needle unit of FIG. 27 further includes a glucose sensor 307 attached to the injection needle 3-11. The glucose sensor 307 penetrates the body of the user when the injection needle 3-11 penetrates the body of the user. As best shown in FIG. 30, which is an enlarged view of FIG. 27, the glucose sensor 307 includes an electrode wire 303 wound around the injection needle 3-11 in the form of a core, an insulating layer 304 coated over the injection needle 3-11 to insulate the injection needle 3-11 from the electrode wire 303, and an enzyme member 302 fitted around a portion of the injection needle 3-11 adjacent to the injection tip while being insulated from the electrode wire 303. Both the enzyme member 302 and electrode wire 303 penetrate the body of the user when the injection needle 3-11 penetrates the body of the user. Leads 305 and 306 are connected to the enzyme member 302 and electrode wire 303, respectively, to electrically connect the enzyme member 302 and electrode wire 303 to a voltage sensing means included in an automatic syringe device to which the injection needle unit is applied. The leads 305 and 306 are buried in the depressing member 3-14. Alternatively, the leads 305 and 306 may be exposed without being buried in the depressing member 3-14.

Meanwhile, the automatic syringe device of FIG. 28, which is adapted to use the injection needle unit of FIG. 27, includes a control configuration for controlling the amount of a liquid medicine, namely, insulin, to be supplied into the body of the user, based on an output from the glucose sensor 307, in addition to an insulin supply configuration identical to that of FIG. 16. The control configuration is also installed in a housing 120 of the automatic syringe device. That is, the automatic syringe device includes a voltage sensing means 310 for sensing an output voltage from the glucose sensor 307, and a control unit 370 for comparing the voltage sensed by the voltage sensing means 310 with a reference voltage, thereby controlling a motor driving unit 350 included in the automatic syringe device to control the supply of insulin. In the illustrated case, the voltage sensing means 310 includes an amplifier 311 for amplifying an output voltage from the glucose sensor 307, a transistor 312 biased by a predetermined level of an output from the amplifier 311, thereby performing a switching function, and an analog/digital converter 313 for converting an output from the transistor 312 into a digital signal. The control unit 370 includes a microcomputer 320 for receiving the digital signal from the analog/digital converter 313 of the voltage sensing means 310 and comparing the received digital signal with a reference value, thereby controlling the entire operation of the control unit 370. The motor driving unit 350 is also included in the control unit 370. The motor driving unit 350 serves to control the rotating speed of a drive motor 352 (FIG. 29) adapted to supply a liquid medicine, under the control of the microcomputer 320. The motor driving unit 350 includes a relay 351 having a movable contact which varies its contact position in accordance with a control signal from the microcomputer 320, and a gear mechanism 353 for varying the rotating speed of the drive motor 352 in accordance with the position of the movable contact. An assistant sensor 354 is installed in the vicinity of the gear mechanism 353 in order to sense the rotating speed of the drive motor 352. The assistant sensor 354 sends a signal, indicative of the sensed rotating speed of the drive motor 352, to the microcomputer 320 which, in turn, controls the motor driving unit 350, based on the signal.

The enzyme member 302 is arranged in the vicinity of the tip of the injection needle 3-11 in such a manner that it penetrates the body of the user when the injection needle 3-11 penetrates the body of the user. The enzyme member 302 serves to sense the blood sugar level in the subcutaneous tissue of the user, thereby inducing electric charge. The electrode wire 303, which is wound around the injection needle 3-11 in the form of a core while being insulated from the injection needle 3-11 by the insulating layer 304, is spaced from the enzyme member 302 by a desired distance. The enzyme member 302 may be made of glucose oxidase which is mainly used for a measurement of blood sugar level.

Although the automatic syringe device of FIG. 28 operates in the same manner as that of FIG. 16 in terms of the injection of insulin, it serves to sense an excessive injection of insulin, thereby automatically control the injection of insulin, as different from that of FIG. 16. That is, when an excessive amount of insulin is injected, the enzyme member (glucose oxidase) 302 integral with the injection needle 3-11 exhibits an accelerated reaction with blood sugar in the subcutaneous tissue of the user. As a result, electric charge is generated around the enzyme member 302. By virtue of the generated electric charge, a flow of current is generated between the enzyme member 302 and the electrode wire 303 insulated from the enzyme member 302. As the blood sugar level in the subcutaneous tissue increases, a decrease in resistance exhibits between the enzyme member 302 and electrode wire 303 insulated from each other, thereby resulting in an increase in the amount of current flowing between the enzyme member 302 and electrode wire 303. The voltage sensing means 310 of the automatic syringe device detects the increased amount of current in the form of a variation in voltage. The voltage sensing means 310 applies the sensed voltage to the microcomputer 320 in the form of a digital value. Of course, the microcomputer 320 is stored with a program for recognizing a voltage abnormality. Based on the result of the recognition carried out in the microcomputer 320, the motor driving unit 350 is controlled. When the relay 351 operates under the control of the microcomputer 320, the polarity and level of a voltage applied to the gear mechanism 353 varies, thereby causing the drive force of the drive motor 352 to vary. Since this technique is well known, its detailed description will be omitted. Thus, the gear mechanism 353 operates to decrease the drive force of the drive motor 352 when a higher blood sugar level is detected whereas it operates to increase the drive force when a lower blood sugar level is detected.

In accordance with the present invention, the gear mechanism 353 has a configuration capable of selecting a desired output level of the drive motor 352. Such a configuration may be embodied using a solenoid (not shown) which is activated by an operation of the relay 351.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides a portable automatic syringe device having a configuration including a separable rotating shaft adapted to provide a drive force to a piston included in the automatic syringe device. The rotating shaft can be separated, along with the piston, from a housing of the syringe device upon refilling a syringe of the syringe device with a liquid medicine. After the re-filling of the liquid medicine, the length of the rotating shaft is manually set. Accordingly, it is possible to easily adjust the initial position of the push means by a manual rotation of the rotating shaft. The rotating shaft is also configured to be rotated only in one direction by a drive force from the motor. Accordingly, the control for the motor is simplified. This results in a reduction in the manufacturing costs. It is also possible to reduce the time taken for the re-filling of the liquid medicine.

Although the automatic syringe device according to the present invention maintains a sealability by providing seal packings for various elements such as covers, plugs and buttons, at least one of those elements (for example, a reset button) is made of a semi-permeable material preventing penetration of moisture while allowing ventilation of air. In this case, it is possible to prevent a vacuum from being generated in the interior of the housing while still maintaining a moisture sealing effect between the housing and reset button. Accordingly, there is no overload in the supply of the liquid medicine.

The present invention also provides an injection needle unit including an "L" shaped injection needle member provided with a curved portion capable of absorbing impact, thereby preventing a breakage of the injection needle member. The injection needle unit also has a protection cap groove for partially receiving a tube-shaped protection cap adapted to protect the injection needle. The protection cap has a through hole receiving the injection needle and having a diameter larger than that of the injection needle. Accordingly, there is no capillarity phenomenon occurring between the inner surface of the needle protection cap and the outer surface of the injection needle when a liquid medicine contained in a syringe is outwardly discharged from the injection needle to vent air existing in the injection needle prior to an injection of the liquid medicine into the body of the user.

The present invention also provides an injection needle unit including a sensor capable of sensing an abnormal blood sugar level generated due to an abnormal injection of a liquid medicine, thereby automatically controlling the amount of a liquid medicine supplied from an automatic syringe device to which the injection needle unit is applied. The sensor is attached to the injection needle in such a manner that it penetrates the body of the user when the injection needle penetrates the body of the user. By virtue of such a sensor, accordingly, it is possible to sense a variation in the blood sugar level in the body of the user due to an excessive injection of the liquid medicine caused by a carelessness of the user. Thus, it is possible to maximize the security of the automatic syringe device.

What is claimed is:

1. An injection needle unit usable in a portable automatic syringe device, the injection needle unit comprising a feeding tube, an "L" shaped injection needle member connected to one end of the feeding tube, a connector connected to the other end of the feeding tube, and a depressing member integrally formed with the injection needle member in such a fashion that the injection needle protrudes perpendicularly from the depressing member, the depressing member being depressed against the skin of a user upon penetrating the injection needle member into the subcutaneous tissue of the user, wherein the injection needle member comprises:

a vertical injection needle provided with a needle tip;

a horizontal connecting rib fitted in said one end of the feeding tube; and a curved portion connected between said injection needle and said connecting rib in such a fashion that it has a quadrant shape extending circumferentially about a center, flush with an upper end of the injection needle, said curved portion having a downward slant portion connected to the connecting rib.

2. The injection needle unit according to claim 1, further comprising:

a protection cap groove for partially receiving a tube-shaped protection cap adapted to protect said injection needle, said protection cap having a through hole for receiving the injection needle, said through hole having a diameter larger than that of the injection needle.

* * * * *